United States Patent [19]
Climie et al.

[11] Patent Number: 5,495,006
[45] Date of Patent: Feb. 27, 1996

[54] ANTIVIRAL POLYNUCLEOTIDE CONJUGATES

[75] Inventors: Shane Climie, Toronto; Michael Ma, Etobicoke, both of Canada

[73] Assignee: Allelix Biopharmaceuticals, Missisauga, Canada

[21] Appl. No.: 24,254

[22] Filed: Mar. 1, 1993

Related U.S. Application Data

[63] Continuation-in-part of Ser. No. 952,404, Sep. 30, 1992, abandoned, which is a continuation-in-part of Ser. No. 766,550, Sep. 27, 1991, abandoned.

[51] Int. Cl.$^6$ .................................................. C07H 21/04
[52] U.S. Cl. ........................... 536/24.1; 536/23.1; 435/5
[58] Field of Search ............................ 536/23.1, 24.1, 536/24.5; 514/44; 435/5

[56] References Cited

U.S. PATENT DOCUMENTS 4,762,779  8/1988  Snitman ..................................... 435/6

FOREIGN PATENT DOCUMENTS

| | | |
|---|---|---|
| 2025335 | 3/1991 | Canada . |
| WO89/02932 | 4/1989 | WIPO . |
| WO89/02931 | 4/1989 | WIPO . |
| WO89/03849 | 5/1991 | WIPO . |
| WO91/06629 | 5/1991 | WIPO . |

OTHER PUBLICATIONS

Antao et al "A thermodynamic study of unusually stable RNA and DNA hairpins" Nucl. Acids Res., 1991, 19:5901.

Ashley et al "Chemical synthesis of oligodeoxynucleotide dumbells" Biochemistry, 1991, 30:2927.

Capobianco et al "One pot solution synthesis of cyclic oligodeoxyribunucleotides" Nucleic Acids Res., 1990, 18:2661.

Cowart et al "A novel combined chemical–enzymatic synthesis of cross–linked DNA using a nucleoside triphosphate analogue".

Biochemistry, 1991, 30:788.

Delling et al Proc. Natl. Acad. Sci., 1991, 88:6234.

DeLuca et al "Physical and functional domains of the herpes simplex virus transcriptional regulatory protein ICP4" J Virology 1988, 62:732.

DiDonato et al "DNA binding and gene regulation by the herpes simplex virus type 1 protein ICP4 and the involvement of the TATA element" J. Virol., 1987, 63:3737.

DiDonato et al "A predictive model for DNA recognition by the herpes simplex virus protein ICP4" J Mol Biol, 1991, 219:451.

Dignam et. al "Accurate transcription initiation by RNA polymerase II in a soluble extract from isolated mammalian nuclei" Nucl. Acids. Res., 1983, 11:1475.

Donis–Keller Nucleic Acids Res., 1980, 8:3133–3142.

Everett et al "Purification of the DNA binding domain of herpes simplex virus type 1 immediate–early protein Vmw175 as a homodimer and extensive mutagenesis of its DNA recognition site" Nucl. Acids Res., 1991, 19(18):4901.

Everett et al "Herpes simplex virus type 1 polypeptide ICP4 bends DNA" Nucleic Acids Res., 1992, 20(6):1229.

Faber et al "Association of the herpes simplex virus regulatory protein ICP4 with specific nucleotide sequences in (List continued on next page.)

Primary Examiner—W. Gary Jones
Assistant Examiner—Scott Houtteman
Attorney, Agent, or Firm—Foley & Lardner

[57] ABSTRACT

The herpes simplex virus encodes ICP4, a DNA binding protein. ICP4-binding duplexed structures having significantly enhanced stability under physiological conditions are described. The structures are provided in the form of polynucleotide conjugates capable of adopting a duplexed structure, in which annealable polynucleotide strands are coupled covalently at one or both ends through a chemical linker which establishes a stabilizing bridge between strands. The present polynucleotide conjugates have therapeutic utility against viral infection as the polynucleotide strands thereof define a binding site for a viral regulatory protein, thereby inactivating the protein and preventing viral replication from occurring.

13 Claims, 7 Drawing Sheets

OTHER PUBLICATIONS

DNA" Nucleic Acids Res., 1986, 14(15):6067.

Kristie et al "DNA–binding site of major regulatory protein α4 specifically associated with promoter–regulatory domains of α genes of herpes simplex virus type 1" Proc. Natl. Acad. Sci. USA, 1986, 83:4700.

Luebke et al "Nonenzymatic ligation of double–helical DNA by alternate–strand triple helix formation" Nucleic Acids Res., 1992, 20:3005.

Ma et al "Design and synthesis of RNA miniduplexes via a synthetic linker approach" Biochemistry 1993, 32:1751.

Matteucci et al "Synthesis and crosslinking properties of a deoxyoligonucleotide containing N6,N6–ethanodeoxyadenosine" Tetrahedron Letters, 1987, 28:2469.

Michael et al "The CNA–binding properties of the major regulatory protein alpha 4 of herpes simplx viruses" Science, 1988, 239:1531.

Muller et al "Binding of the herpes simplex virus immediate–early gene product ICP4 to its own transcription start site" J. Virol., 1987, 61:858.

Petric et al. "Ligation with T4 RNA ligase of an olgodeoxyribonucleotide to covalently–linkesd cross–sectional base–pair analogues of short, normal, and long dimensions" Nucleic Acid Res., 1991, 19:585.

Prakash et al "Structural effects in the recognition of DNA by circular oligonucleotides" J. Am. Chem. Soc., 1992, 114:3523.

Rao et al "Synthesis of cyclic oligodeoxyribonucleotides via the filtration approach" Nucleic Acids Res., 1989, 17:8221.

Roy et al Genes Dev., 1990, 4:1365.

Salunkhe et al "Control of folding and binding of oligonucleotides by use of a nonnucleotide linker" J. Am. Chem. Soc., 1992, 114:8768.

Scaringe et al "Chemical synthesis of biologically active olgoribunucleotides using β–cyanoethyl protected ribunucleoside phosphoramidites" Nucl. Acids Res., 1990, 18:5433–5441.

Seela et al Nucleic Acids Res., 1987, 15:3113–3129.

Shepardt et al "trans–Dominant inhibition of herpes simplex virus transcriptional regulatory protein ICP4 by heterodimer formation" J. Virology, 1990, 64(8):3916.

Sumner–Smith et al J. Virol., 1991, 65:5196.

Weeks et al Science, 1990, 249:1281.

Uhlmann et al "Anrtisense oligonucleotides: A new therapeutic principle" Chemical Rev., 1990, 90:543.

Usman et al "Automated chemical synthesis of long oligoribonucleotides using 2'–O–silylated ribonucleoside 3'–O–phosphoramidites on a controlled–pored glass support: synthesis of a 43–nucleotide sequence similar to the 3'–half molecule of an *Escherichia coli* formynethionine tRNA–nucleotide sequence similar to the 3'–half molecule of an *Escherichia coli* formylnethionine tRNA–nucleotide sequence similar to the 3'–half molecular of an *Escherichia coli* formylnethionine tRNA" J. Am. Chem. Soc., 1987, 109:7845–7854.

○P = INTERNAL PHOSPHATE

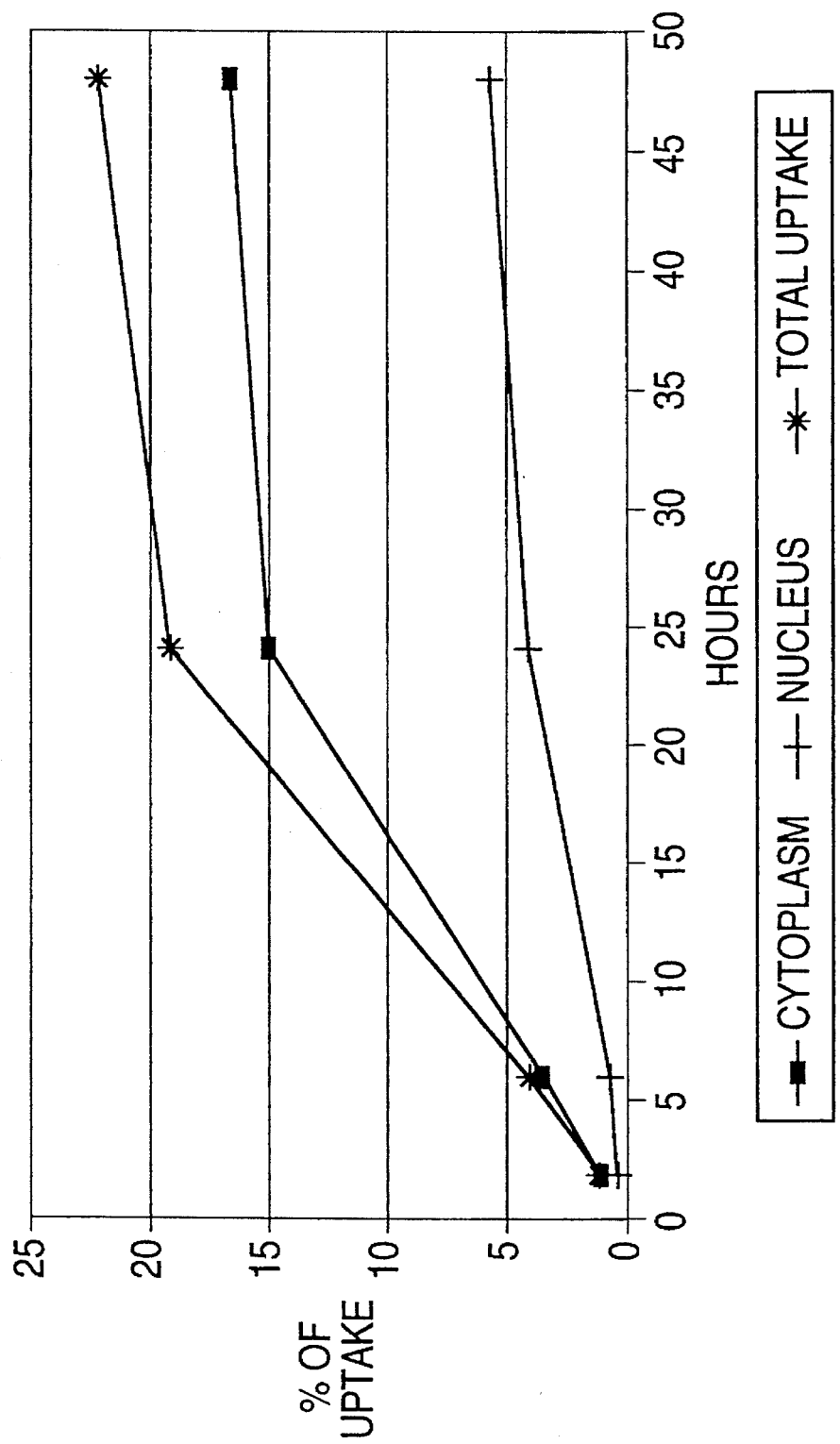

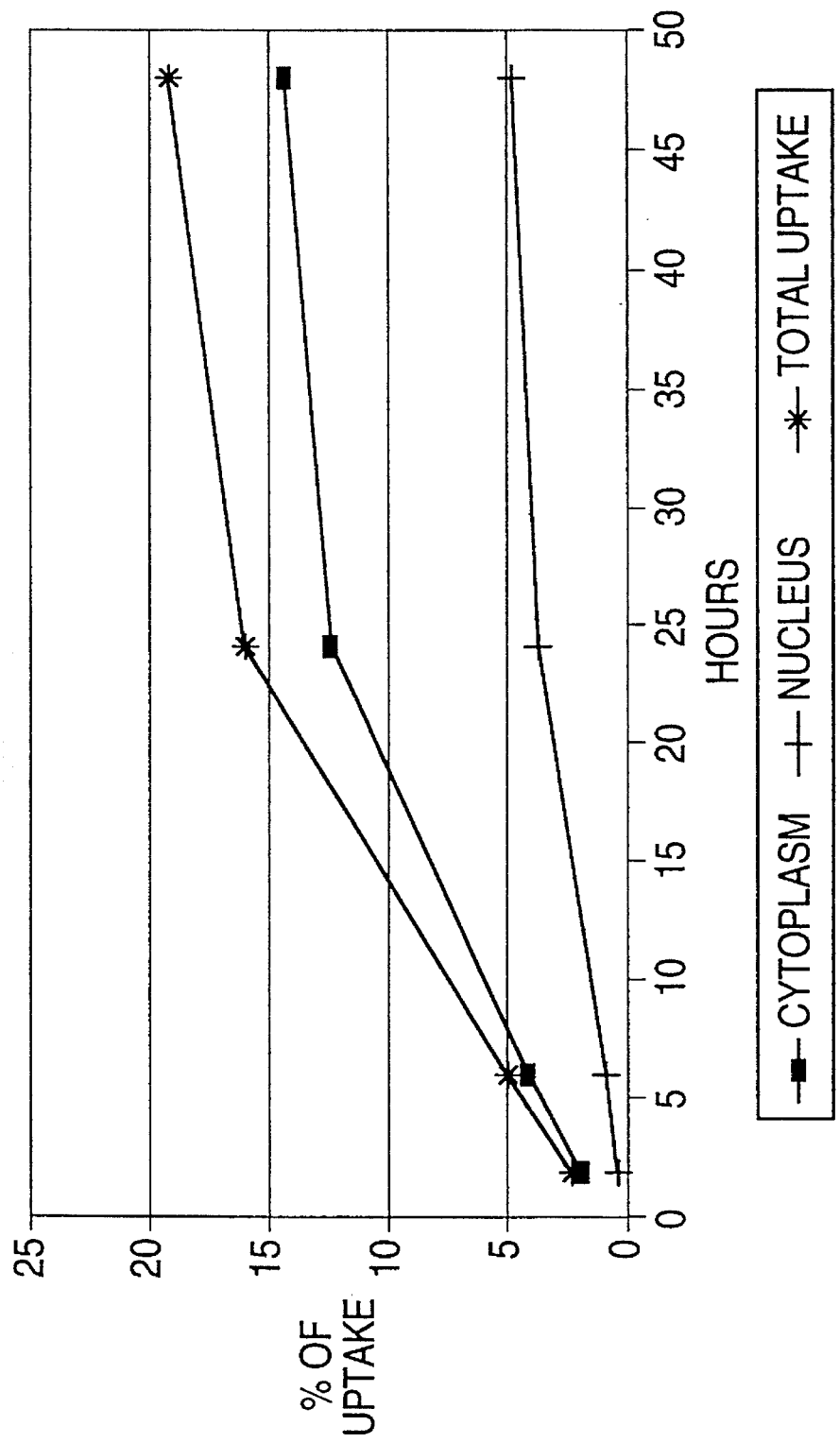

ANTIVIRAL POLYNUCLEOTIDE CONJUGATES

CROSS-REFERENCE TO RELATED APPLICATIONS

This application is a continuation-in-part application of U.S. patent application Ser. No. 952,404, filed on Sep. 30, 1992, now abandoned which is a continuation-in-part of U.S. patent application Ser. No. 766,550, filed on Sep. 27, 1991, now abandoned, the contents of both of which are incorporated herein by reference.

FIELD OF THE INVENTION

This invention relates to the field of nucleic acid chemistry. More particularly, the invention relates to polynucleotide conjugates that adopt a ligand binding duplexed structure, to the production of such conjugates particularly via automated synthesis techniques, and to their use in therapeutic, diagnostic and other applications.

BACKGROUND TO THE INVENTION

The ability to regulate cellular processes at the genetic level in a highly selective and therapeutic manner is now offered by various forms of oligonucleotide-based pharmaceuticals. These oligonucleotides are designed according to their nucleic acid sequence to arrest genetic processes by binding disruptively to a selected genetic target, usually a viral gene or a human gene that is associated with a particular disease state such as cancer or a condition such as inflammation. Transcription of an undesired gene can, for example, be arrested by a synthetic oligonucleotide that hybridizes selectively to a control region or coding region of that gene; similarly, translation of an undesired protein can be arrested using an oligonucleotide that hybridizes with a control region or coding region of the messenger RNA encoding that protein. Many of the problems associated with the practical use of such oligonucleotide-based therapeutics, such as cell uptake, stability, and cost of production, have been resolved by recent advances in nucleic acid chemistry.

These current strategies contemplate principally the use of oligonucleotides which, in order to hybridize to their intended nucleic acid target, are necessarily single-stranded complements of that target. That is, oligonucleotides intended for use as pharmaceuticals are designed currently to bind as single-stranded entities to other nucleic acid targets, whether single-stranded messenger RNA or single stranded DNA (the so-called "sense" and "anti-sense" approaches, reviewed for example by Uhlmann et al., 1990, Chemical Rev., 90:543) or, as has more recently been proposed, to double stranded DNA (the "triplex" approach). These approaches neglect other cellular targets that are at least equally attractive in the overall development of gene regulating therapeutics. More particularly, it would be desirable to provide oligonucleotide agents capable of interfering with interactions specifically between nucleic acids and their ligands, particularly their protein ligands, which play a role in infectious and other disease states.

The feasibility of designing oligonucleotides that interfere with a protein/nucleic acid interaction of therapeutic interest is complicated in that, in the majority of instances, the protein recognizes a nucleic acid that is double-stranded in structure; and further in that double stranded oligonucleotides of the small size necessary for pharmaceutical applications, for uptake by the cell, and for stability, are highly unstable and must typically be incubated under temperatures so cold and/or salt concentrations so high as to make subsequent study and use of the duplexed structures impractical.

It is a principle object of the present invention to provide polynucleotide conjugates that are capable of adopting a ligand-binding duplexed structure which has enhanced stability, i.e. enhanced physical or chemical stability.

A further object of the present invention is to provide stability-enhanced duplexed polynucleotide conjugates having anti-viral activity.

SUMMARY OF THE INVENTION

Accordingly, there is provided by the present invention a family of duplex-forming compounds, herein referred to as polynucleotide conjugates, which comprise a first polynucleotide strand having an end, a second polynucleotide strand having an end which is capable of annealing with the first polynucleotide strand to form a ligand binding structure, and a chemical linker which is coupled between ends of the polynucleotide strands to form a bridge permitting the conjugate to form a ligand-binding duplexed structure.

The stability-enhanced duplexed structures of the invention are provided in the form of linear polynucleotide conjugates, conforming to the general formula:

X—L—Y            (I)

wherein:

X and Y are polynucleotide strands capable of annealing to define a ligand binding site for a protein ligand that regulates viral gene expression; and L is a first chemical linker coupled covalently between a pair of adjacent ends of said polynucleotide strands to form a duplexed ligand-binding structure.

Compounds conforming to the general formula (I) are linear polynucleotide conjugates and are most conveniently produced using automated polynucleotide synthesis techniques. For this purpose, the present invention further provides analogues of the chemical linkers in bifunctional form for incorporation between nucleotide strands using established nucleotide coupling protocols.

The stability-enhanced duplexed structures may also be in the form of cyclic polynucleotide conjugates, which conform either to the general formula:

(IIa)

wherein:

X is a polynucleotide having a 5'terminus and a 3'terminus;

Y is a polynucleotide capable of annealing with X and having a 3'terminus and a 5'terminus;

Z is a polynucleotide coupled covalently between the 5'terminus of X and the 3'terminus of Y; and L is a chemical linker coupled between the 3'terminus of X and the 5'terminus of Y, to form a bridge permitting the conjugate to form a ligand-binding duplexed structure; or to the general formula:

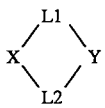

(IIb)

wherein:

X and Y are as defined above; and

L1 and L2 are independently selected chemical linkers coupled, respectively, between the 3'terminus of X and the 5'terminus of Y and the 5'terminus of X and the 3'terminus of Y, to form chemical bridges permitting the conjugate to form a ligand-binding duplexed structure.

The cyclic polynucleotide conjugates of the invention, as represented by formulae IIa and IIb are suitably prepared by synthesizing the linear analogue thereof using the automated nucleotide coupling techniques appropriate for linear conjugates of formula (I) and then closing the linear conjugate typically using either chemical or enzymatic means, to form the cyclic polynucleotide conjugate.

In valuable embodiments of the invention, the polynucleotide conjugate is one capable of adopting a duplexed structure that is recognized by i.e. binds with, a target ligand that is a protein, for example a protein capable of regulating gene expression. Thus, in accordance with one aspect of the present invention, a duplex-forming polynucleotide conjugate comprising a pair of chemically linked polynucleotide strands capable of annealing to define a binding site for a protein that regulates viral gene expression is provided.

In accordance with another aspect of the present invention, there is provided a pharmaceutical composition which comprises a ligand-binding polynucleotide conjugate and a pharmaceutically acceptable carder. In a specific embodiment of the present invention, the composition includes a polynucleotide conjugate characterized by an affinity for binding with a protein which regulates viral gene expression, e.g. expression of a herpes simplex virus gene.

These and other aspects of the present invention will be described in greater detail by reference to the accompanying drawings in which:

BRIEF REFERENCE TO THE DRAWINGS

FIGS. 1(a)–(d) and 2(a)–(f) illustrate duplexed structures of various conformations and configurations that can be stabilized in accordance with the present invention. Solid lines illustrate polynucleotide structure and hatching identifies the nucleotide components. The symbol "." is used to indicate hydrogen-bonded base-pairing within annealed regions of the polynucleotide strands, and the symbol L is used to indicate location of the chemical linker;

FIGS. 8 and 9 illustrate graphically the cellular uptake of specific polynucleotide conjugates of the invention.

DETAILED DESCRIPTION OF THE INVENTION

Figure 2F:
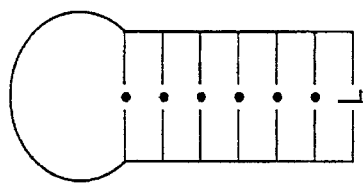
Figure 2E:
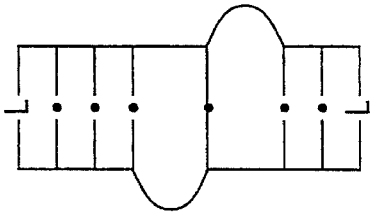
Figure 2D:
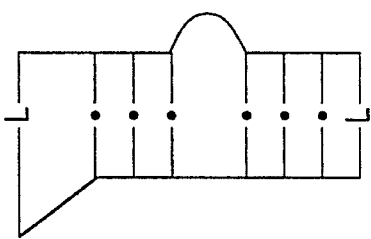
Figure 2C:
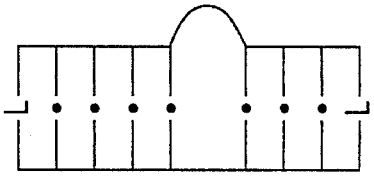
Figure 2B:
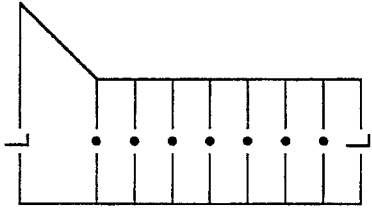

The present invention provides polynucleotide conjugates characterized by the properties of ligand binding and enhanced stability. In the present specification, the term "enhanced stability", unless otherwise stated, refers to the superior thermal stability of a polynucleotide conjugate relative to its unlinked counterpart, as measured using melting temperature (Tm) assays established in the art. The term "ligand" is used herein with reference to agents that bind measurably, in the context of an assay appropriate for that measurement, to nucleic acid structures, principally double- stranded structures but also single-stranded structures. The term ligand is thus intended to embrace such agents as proteins, including proteins that regulate genetic processes such as transcription and translation, as well as non-protein entities including but not limited to intercalating agents and nucleic acid binding antibiotics as well as other nucleic acids. The term "ligand-binding" is thus used with reference to polynucleotide conjugates that adopt a structure that is bound measurably by a ligand against which the conjugate is targeted.

In providing duplexed structures of enhanced stability, the present invention permits the use of double-stranded polynucleotide structures in a wide variety of applications not previously possible as a result of prior stability problems. Because the chemically linked duplexed structures of the present invention are substantially more stable than their unlinked counterparts under physiological conditions, for example, therapeutic applications for duplexed structures are now feasible. In addition, it will be appreciated that the stability-enhancing effect of the chemical linker can be exploited to eliminate polynucleotide regions that are otherwise required to permit formation and maintenance of the desired duplexed structure in vitro and in vivo. Further, the chemical linkers employed to form the present polynucleotide conjugates are substantially resistant to nuclease digestion, a contributing factor to the instability of unlinked polynucleotide fragments in vivo. Thus, polynucleotide conjugates according to the present invention are advantageously of a molecular weight that is pharmaceutically appropriate, while sustaining a stability comparable to that of endogenous polynucleotides that naturally exist in vivo.

To stabilize polynucleotides, the present invention applies the strategy of incorporating a chemical linker between one or both ends of polynucleotide strands capable of forming a duplexed structure. It will be understood that in order to form a duplexed structure, such strands will share at least a region of sequence complementarity sufficient to permit annealing of the strands. The individual polynucleotide strands forming the duplex may consist of RNA or DNA monophosphates or synthetic analogues thereof, or mixtures thereof. Synthetic analogues may include, for example, those analogues which incorporate variations in the base constituent, such as thio- and aza-substituted bases, variations in the sugar constituent, such as alkyl- or halo-substituted ribose and arabinose equivalents, or variations in the monophosphate group, such as phosphorothioates and dithioates, methyl phosphate and methyl phosphonates, phosphoramidates and phosphoramidites and the like. The polynucleotide strand may also incorporate a non-nucleic acid component, to the extent that duplex formation and ligand-binding are not substantially impaired.

The polynucleotide strands forming the duplex may be of the same or different lengths, and each may incorporate any number of nucleotides in a range of from about 2 to a maximum that is dictated largely by the limits of automated gene synthesis techniques. Strands consisting of not more than about 200 nucleotides, for example not more than about 100 nucleotides, will derive the most benefit from the stabilizing effect of the chemical bridge, however. Preferably each of the polynucleotide strands consists of from 3 to 100 nucleotides, and more preferably, from about 4 to 50 nucleotides. Polynucleotide strands that are capable of annealing, and which can thus benefit from the linker strategy herein described, include those strands that anneal in an anti-parallel orientation, i.e. consist of beta nucleotides, and strands that consist of alpha nucleotides in one strand and beta nucleotides in the other strand, and thus can anneal in the parallel orientation. In the simplest case, the polynucleotide strands will be precisely complementary and equivalent in length, and will anneal along their entire length, to form a completely double-stranded duplexed structure. It will be appreciated however, that with the aid of a chemical linker, duplexed structures having a variety of conformations and configurations can be stabilized.

In accordance with a specific embodiment of the present invention, the number of nucleotides in the polynucleotide strands of the conjugate is limited to a number that bestows on the conjugate utility as an anti-viral, for example, in the treatment of a herpes simplex virus infection. Generally, the number of nucleotides in such an anti-ritual conjugate will be that number sufficient to define a binding site for a targeted viral regulatory protein while desirably omitting nucleotides that are unnecessary for that purpose. The polynucleotide strands may include the same number of nucleotides as exist in the natural binding site of the targeted protein, or alternatively, the strands may include a different number of nucleotides than the number in the natural binding site provided that there is a binding interaction between the protein and the polynucleotide conjugate.

Some of the duplexed structures currently contemplated are illustrated schematically in FIGS. 1 and 2, to which reference is now made. Other structures or combinations may also be stabilized in accordance with the present invention, of course. As shown schematically in FIG. 1, duplexed structures that can be generated as linear polynucleotide conjugates of the general formula (I) comprise a single chemical linker incorporated at one end of the duplex structure. FIG. 1(a) illustrates the simplest case which, as described above, incorporates a linker at one end of precisely complementary polynucleotide strands, which anneal along their entire length to form a fully double stranded duplex structure. FIG. 1(b) illustrates the case in which the annealable strands incorporate a terminal mismatch, which results in a non-annealing "fork" structure at one end of the duplex. FIG. 1(c) illustrates the situation in which one polynucleotide strand incorporates an internal, mismatched region resulting in a non-annealed bulge. FIG. 1(c) further illustrates that polynucleotide strands of different length can also be linked, according to the present invention, as is further shown by the structure of FIG. 1(d).

Similarly, duplexed structures that can be generated as cyclic polynucleotide conjugates of the formula (IIa) and (IIb) may also adopt various conformations and configurations. As shown in FIG. 2(a), the simplest case is again the situation where precisely complementary strands are coupled using chemical linkers at both ends. Similarly, the forked structure shown in FIG. 2(b) can also be linked at both ends, as may the bulged structure shown in FIG. 2(c). The forked structure of FIG. 2(b) also illustrates that chemical linkers of different length may be used to bridge polynucleotide strands in the annealing relationship desired for duplex formation. Duplexes that are more elaborate in structure can also be stabilized if desired, as shown for example in FIGS. 2(d) and 2(e). The duplexed structures appearing in FIGS. 2(a)– (e) are intended to be embraced by the general formula II(b) recited hereinabove.

Figure 2A:
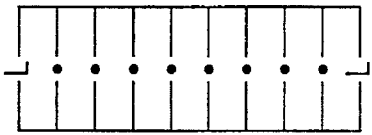
Figure 1D:
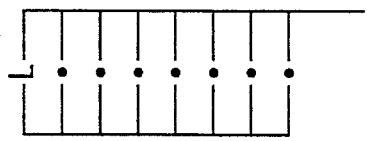
Figure 1C:
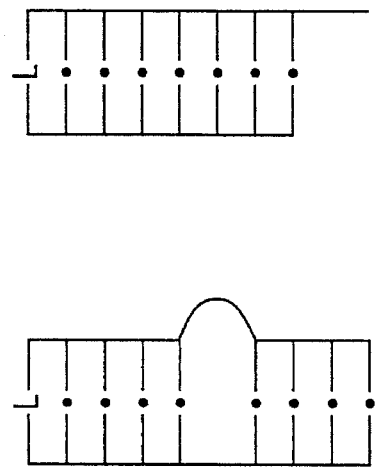
Figure 1B:
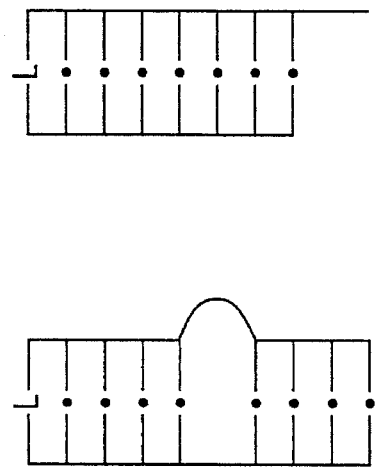
Figure 1A:
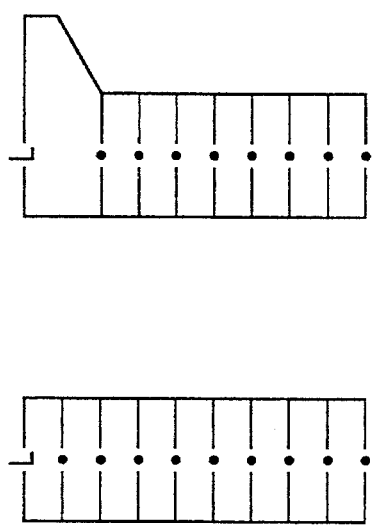

The duplexed structure illustrated in FIG. 2(f) represents a special but important case, in which a cyclic duplexed structure is created by incorporation of a single chemical linker, as embraced generally by the formula II(a) recited hereinabove. In this case, Z is represented by the polynucleotide 'loop' bridging the annealed polynucleotide strands. As will be described herein, such structures exist naturally in the unlinked form, occurring predominantly in the form of RNA "hairpins" that regulate the expression of certain viral and other genes through a protein-binding interaction. Such duplexed structures are accordingly ideal as targets for therapeutic application, when in their chemically linked form.

Figure 3:
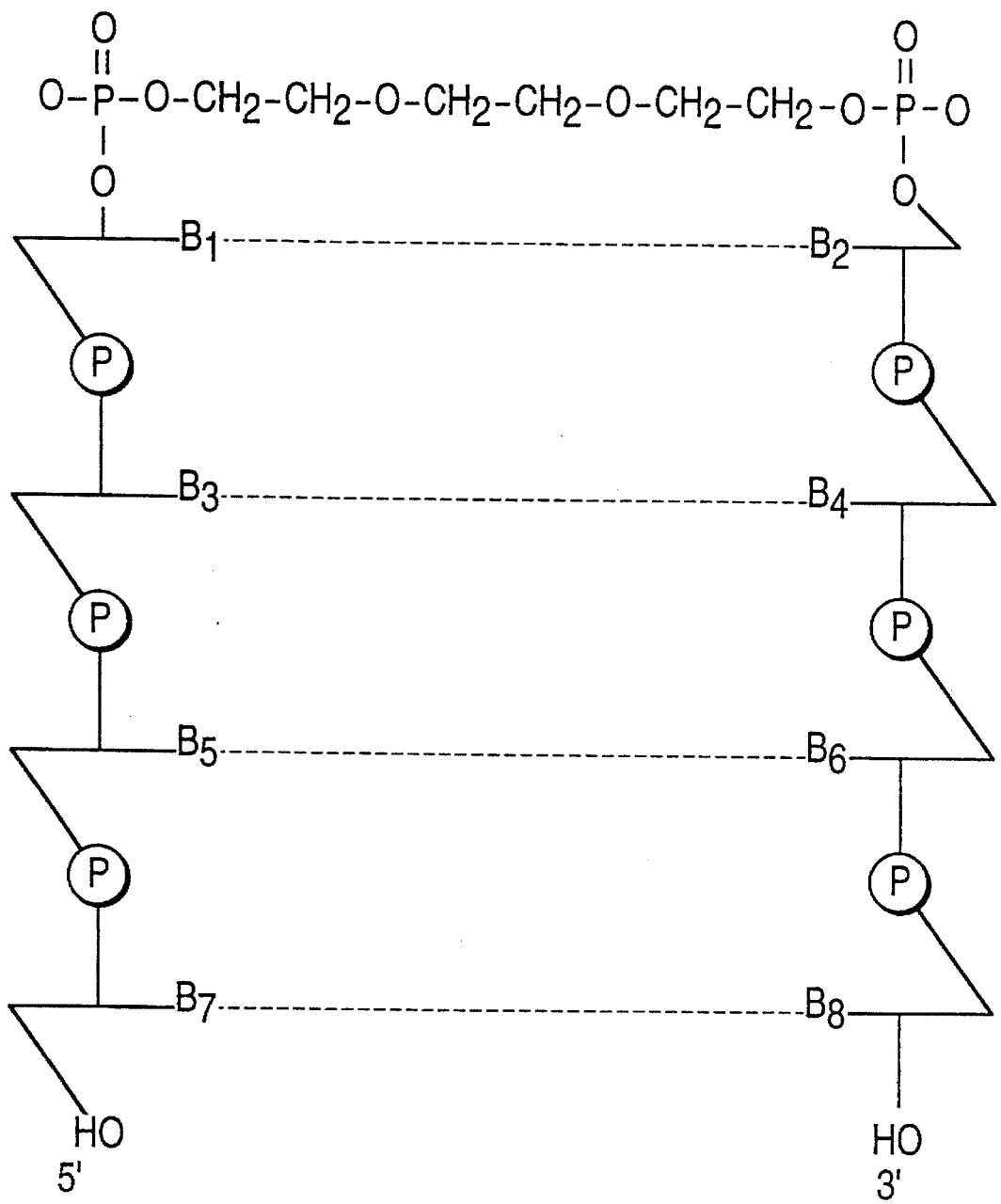
FIG. 3 shows incorporation of a specific linker of the present invention between polynucleotide strands.

As noted above, the linking of duplex-forming polynucleotide strands is achieved by covalently coupling the chemical linker between neighbouring termini of the polynucleotide strands, either between the 5' terminus of one strand and the 3' terminus of the other, or vice versa. As is shown in FIG. 3, linkers are most suitably incorporated by coupling between the monophosphate or analogous groups borne at the termini. It is to be understood that the chemical linkers used in the present invention are synthetic chemical linkers as opposed to polynucleotide-based linkers of the type represented by substituent Z in Formula (IIa).

The chemical linker has a length selected ideally to preserve the desired annealing relationship between strands at the location of the linker. Since numerous duplex conformations can be stabilized using the linker, linkers of similarly various lengths can be incorporated for this purpose. Generally, the length of the linker will correspond to the length of a linear chain alkane comprising from about three carbon atoms ($C_3$) to about 30 carbon atoms ($C_{30}$). In particular, it has been found that a chemical linker having a length equivalent to a linear chain alkane consisting of from 7 to 20 carbon atoms, suitably 8 to 15 carbon atoms and desirably 9 to 12 carbon atoms, is appropriate to link polynucleotide strands at an annealed location. For coupling of strands at a mismatched, non-annealed location, a chemical linker having a length equivalent to greater than about 10 carbon atoms, for example having a length in the range from about 10 carbon atoms to about 20 carbon atoms, is suitable for incorporation.

The optimal linker length at an annealed or non-annealed location is generally that length which corresponds to the distance between the polynucleotide strands to be linked. In approximate terms that length may be in a range from about 10 Å to about 15 Å. The distance between strands will vary depending of course on the nature and composition of the polynucleotide strands, i.e. whether the strands include ribonucleotides or deoxyribonucleotides. Generally, the distance between ribonucleotide strands is less than the distance between deoxyribonucleotide strands. Accordingly, the optimal length of linkers for use in joining ribonucleotide strands may be less than the optimal length of linkers suitable for use in joining deoxyribonucleotide strands. Since functional groups are also incorporated at the ends of the linker to permit coupling with nucleotides, as described below, determination of desired linker length should be made with this in mind.

The chemical composition of the linker can vary widely, provided that consideration is given to the need for stability under physiological conditions and under the conditions encountered during nucleotide coupling protocols. The linker may contain functional groups, for example to serve as attachment sites for other molecular entities, provided that suitable protecting groups are employed during synthesis of the polynucleotide conjugate. A key requirement in choosing a linker composition is to retain the length appropriate for duplex formation. In this connection, it will be appreciated that side chains are acceptable, particularly in the central region of the linker. Moreover, the desired length of the linker can be achieved using carbon atoms or carbon atoms in combination with heteroatoms, including oxygen, sulfur, phosphorus, nitrogen, etc. Also, cyclic structures can be incorporated, including benzene and heterocycles such as piperidine, piperazine or pyridine coupled within the linker chain either through a carbon center or a heteroatom. It will also be appreciated that the chemical composition of the linker can be manipulated through component selection to alter hydrophobicity or hydrophilicity, if desired, particularly for the purpose of altering solubility, cellular uptake, and to facilitate dosage formulation where therapeutic applications are being considered.

For incorporation between polynucleotide strands, the chemical linkers are provided in the form of bifunctional analogues, bearing terminal functional groups that, desirably, are amenable to protection and derivatization that adapts them for coupling using the same protocols applied conventionally for automated nucleotide coupling. Such bifunctional linker analogues conform to the general formula:

R—linker—R' wherein, most suitably, R and R' are independently selected from among the group consisting of —OH, —SH, —NH and functional equivalents of these groups. In order that the linkers can be incorporated, and the polynucleotide conjugates synthesized, using the currently most practical phosphoramidite approach, as described in more detail in the specific examples herein, the linker is preferably one in which at least one of R and R' is OH. Most preferably, both R and R' are OH.

Bifunctional linkers suitable for use in coupling polynucleotide strands at an annealed location are exemplified by, and include:

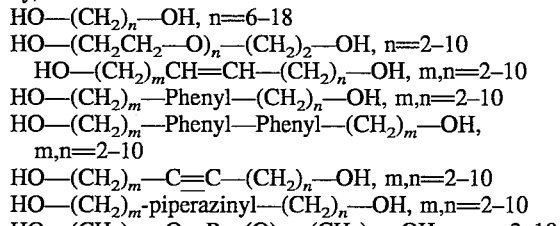

HO—$(CH_2)_n$—OH, n=6–18
HO—$(CH_2CH_2$—O$)_n$—$(CH_2)_2$—OH, n=2–10
HO—$(CH_2)_m$CH=CH—$(CH_2)_n$—OH, m,n=2–10
HO—$(CH_2)_m$—Phenyl—$(CH_2)_n$—OH, m,n=2–10
HO—$(CH_2)_m$—Phenyl—Phenyl—$(CH_2)_m$—OH, m,n=2–10
HO—$(CH_2)_m$—C≡C—$(CH_2)_n$—OH, m,n=2–10
HO—$(CH_2)_m$-piperazinyl—$(CH_2)_n$—OH, m,n=2–10
HO—$(CH_2)_m$—O—P—$(O)_2$—$(CH_2)_n$—OH, m,n=2–10

It will be appreciated that linkers of appropriate length may also be formed in situ i.e. during conjugate synthesis, by coupling selected linkers sequentially to extend linker length as desired.

The polynucleotide conjugates of the present invention may be synthesized using the techniques described in U.S. co-pending patent application Ser. No. 952,404, the contents of which are incorporated herein by reference. Specifically, the polynucleotide strands may be synthesized by applying conventional techniques of polynucleotide synthesis and using commercially available polynucleotide synthesizing devices or "gene machines".

Various strategies of solution and solid phase techniques may be employed in the synthesis of polynucleotide strands including the phosphotriester method, the solid phase H-phosphonate method or the solid phase phosphoramidite method. The latter method generally comprises sequential nucleotide coupling in the 3'–>5' direction by deprotecting fully protected nucleotides, the initial nucleotide being releasably coupled to solid support. The 5' primary hydroxyl group of nucleotide deoxyribose sugars is protected with an ether moiety which is removed prior to reaction with a mild protic acid, while the 3' secondary hydroxyl group is protected using a phosphoramidite group and subsequently activated for coupling with a weak acid. Amino functionalities present on the nucleotides are additionally protected using, for example, the isobutyryl or benzoyl groups which are removable upon completion of the synthesis by ammoniolysis.

In the case of conjugates which are linked at one end only, the chemical linker may be coupled to the polynucleotide strands to form the conjugate of the present invention during the synthesis of the polynucleotide using the mechanism of protection and deprotection as outlined above. Thus, to produce a linear polynucleotide conjugate, the first nucleotide of a polynucleotide strand is bound to a resin solid support, treated with protic acid to remove the 5' hydroxyl protecting group and coupling of the 3' hydroxyl of the next nucleotide is activated to result in 3'–>5' coupling. The coupling is completed by an oxidation reaction. At the desired point in the synthesis, the protected linker is incorporated using the same deprotection/activation scheme and the synthesis is continued until the polynucleotide strand complementary to the first polynucleotide is completed. The conjugate is then released from the support, the bases are deprotected, and the conjugate is purified using purification techniques well established in the art. The conjugate assumes a linear double-stranded configuration in which the polynucleotide strands are annealed. FIG. 3 provides the chemical structure resulting from the covalent coupling of a specific triethylene glycol-derived linker, between polynucleotides. It will be noted that the linker is coupled to the termini of the nucleotides through the monophosphates borne on the respective 5' and 3' hydroxyl groups.

To synthesize a cyclic conjugate, the double-stranded polynucleotide is synthesized as described for linear conjugates comprising a single linker. The open end of the resulting conjugate is then linked using either chemical reaction or enzymatic ligation. Several suitable methods exist by which the double-stranded polynucleotide may be chemically cyclized using condensation agents such as cyanogen bromide (Prakash et al., J. Am. Chem. Soc., 1992, 114:3523), water-soluble carbodiimide (Ashley et al., Biochemistry, 1991, 30:2927), and N-cyanoimidazole (Luebke et al., Nucleic Acids Res., 1992, 20:3005). These techniques are used with a fully deprotected polynucleotide. In contrast, a polynucleotide selectively deprotected to render a free 5'—OH and a 3'-phosphate is cyclized using 1-( 2-mesitylenesulfonyl)- 3-nitro-1,2,4-triazole (MSNT) as the condensation reagent (Rao et al., Nucleic Acids Res., 1989, 17:8221). Further, Capobianco et al. (Nucleic Acids Res., 1990, 18:2661) describe a phosphotriester approach for generating a cyclic polynucleotide directly on a solid-support. Cyclization by enzymatic ligation includes the steps of incubating the polynucleotide under annealing conditions and then treating with DNA ligase. The cyclic conjugates resulting from the reaction are recovered and purified using conventional techniques.

To provide duplexed structures that, in accordance with the present invention, exhibit not only enhanced stability but also a ligand binding property, the polynucleotide strands to be linked during synthesis are selected in terms of their nucleic acid sequence, and based on knowledge of the particular nucleic acid sequence to which a target ligand binds. It will be appreciated that selection of strands appropriate for desired ligand binding can be guided by the vast scientific literature dealing with protein/nucleic acid interactions. In those instances where a binding domain of specific interest remains to be identified, it will be appreciated that the mapping of that domain can be achieved using conventional approaches, so that a specific binding sequence can be elucidated. The strategy herein described can in fact facilitate such mapping, by permitting the synthesis of a series of stabilized duplexed structures representing putative ligand binding domains that can then be screened for ligand binding activity using, for example, mobility shift assays.

The polynucleotide conjugates are preferably employed to mimic naturally occurring duplexed structures, and the polynucleotide strands in the conjugate are accordingly selected to correspond in sequence to a naturally occurring duplex counterpart. Conceivably, any duplexed region of a naturally occurring gene or other genetic element can be duplicated in stability-enhanced form, in accordance with the present invention.

Ligands of potential interest include those proteins which on binding to their natural, nucleic acid target, directly or indirectly, influence the utilization or fate of that nucleic acid target. Examples of such proteins include: ribo- and deoxyribonucleoprotein complexes; gene regulatory proteins such as repressors, activators and transactivators, etc.; proteins involved in the modifications and fate of mRNA molecules, including splicing, polyadenylation, capping, nuclear export, translation, degradation, etc.; proteins involved in the assembly and utilization of other RNA or ribonucleoprotein structures such as ribozymes, tRNA synthetases, splicing complexes, etc. In all cases, the essential feature of such proteins is that they recognise particular nucleic acid structures on the basis of their conformation and/or sequences; embodiments of this invention would provide effective analogues when they maintain some or all of such requirements.

In one aspect of the present invention, the gene products of the "immediate-early" genes of the herpes simplex virus are targeted by specific polynucleotide conjugates. The term "herpes simplex virus", HSV, is used herein to encompass herpes simplex virus type I (HSV-I) and herpes simplex virus type II (HSV-II). The immediate-early gene products of HSV are expressed upon viral infection and have been shown to be essential in the transactivation of subsequently expressed genes commonly known as "early" and "late" genes. The polynucleotide strands of present conjugates incorporate a nucleotide sequence that defines a binding site for a targeted immediate early transcriptional regulatory protein of herpes simplex virus (HSV). Specifically targeted are those immediate early proteins which are required for replication of the virus in an infected host cell and which perform their biological function by interacting with a specific nucleotide sequence. Thus, encompassed within the scope of suitable HSV protein targets are the immediate-early (IE) transcriptional regulatory proteins of HSV-1 and HSV-2 denoted ICP0, ICP4, ICP22, ICP27 and ICP47. The IE transcriptional regulatory proteins ICP4 and ICP27 are particularly suitable targets for the present polynucleotide conjugates, and most desirably, the ICP4 regulatory protein is targeted.

In a specific embodiment of the present invention, polynucleotide strands which hybridize to define a DNA-binding site for the ICP4 regulatory protein were linked with a chemical linker to form an anti-HSV polynucleotide conjugate. One such polynucleotide conjugate (III) is illustrated below incorporating a 22-deoxyribonucleotide fully hybridized sequence (SEQ ID NOS 6 and 7):

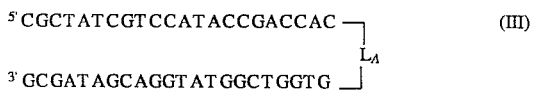

(III)

Another such anti-HSV polynucleotide conjugate (IV) incorporating a 13-deoxyribonucleotide fully hybridized sequence encoding an ICP4 DNA-binding site is illustrated as follows (SEQ ID NOS 8 and 9):

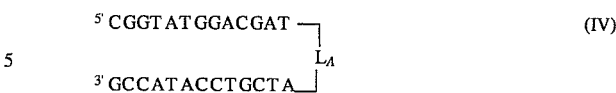

(IV)

The polynucleotide strands comprising conjugates (III) and (IV) were synthesized using the solid phase phosphoramidite method, and the linker, $L_A$, was incorporated at the mid-point of the polynucleotide synthesis using the same mechanism of protection and deprotection. In this case, $L_A$ was the linker $HO—(CH_2)_9—OH$. Prior to its incorporation, one end of the linker was protected with a dimethoxytrityl group as described in detail in Example 1. The synthesis occurred in the 3'→5' direction until one strand of the double-stranded polynucleotide was synthesized, the linker was incorporated and then the polynucleotide synthesis was resumed to completion of the conjugate.

Polynucleotide conjugates (III) and (IV) were found to inhibit HSV-1 as determined using a plaque reduction assay. Specifically, monolayers of cells were pretreated by incubation with one of conjugates (III) and (IV), infected with various concentrations of HSV-1 (measured by plaque forming units, PFU) and the infected cells were then incubated in the presence of conjugate. Following incubation with the conjugate, the cells were stained using the conventional crystal violet staining method. Those portions of the cell monolayer appearing as clear, unstained areas were identified as dead, virally-infected cells (i.e. plaques), while those areas stained purple indicated viable cells. Thus, inhibition of the virus was determined by counting, using a dissecting microscope, the number of plaques. The number of plaques on a plate incubated in the presence of conjugate was compared to the number of plaques on a control plate incubated in the absence of conjugate and the extent of viral inhibition was thus determined.

To illustrate further the ability of the present polynucleotide conjugates to regulate viral gene expression, a conjugate defining a binding site for the tat protein of the human immunodeficiency virus (HIV) was prepared. Through interaction with the RNA hairpin structure known as Tar, the tat protein mediates a rapid increase in the production of the viral components required for HIV replication, which in turn leads to the onset of AIDS. It has been suggested that agents capable of interfering with the tat/Tar interaction would be useful in arresting HIV replication, and thus efficacious in the treatment of AIDS. The present invention accordingly provides a polynucleotide conjugate which mimics the Tar structure, adopting a duplexed structure having a binding affinity for tat. Such binding affinity is revealed using standard mobility shift assays, in tat/Tar complexes, and thus tat-binding, is revealed by altered migration relative to tat and Tar alone (see Roy et at, infra). The chemical structure of a suitable polynucleotide conjugate for this purpose is described in the examples herein. It will be appreciated, however, that sequence variation can be tolerated without loss of tat binding affinity, and such variations in which tat binding is retained are within the scope of the present invention.

Other viral processes can also be targetted for therapeutic interference using the stabilized duplex structures of the present invention. For example, in HIV, besides the TAR structure, the duplexed RRE RNA structure required to regulate splicing and the duplexed $tRNA_{Lys3}$ structure used as a primer for reverse transcription can be mimicked using the present strategy. There may also be produced duplexed structures which bind other regulatory protein ligands, for example those known to exist in human pathogenic viruses, including: the P protein of Hepatitis B virus (HBV); the VP16 protein of HSV; the E1 and E7 proteins of Papilloma virus (HPV); the BZLF1 and EBNA-1 proteins of Epstein Barr virus (EBV); as well as additional proteins in these and other viruses.

Formulation and administration of the compounds herein described, and indeed any annealed polynucleotide structures having pharmaceutical utility, can be accomplished in accordance with procedures routinely applied to aqueous-soluble compounds. Thus, for parenteral administration, buffered saline solutions are acceptable. Where a reduction in administration frequency is desirable, timed-release polymeric compositions which do not unfavourably chemically modify the compounds are acceptable. Modification of pharmacokinetic properties, especially distribution, are achieved, for instance, through the use of liposomal or cationic lipid formulations.

In accordance with a preferred embodiment of the present invention, a pharmaceutical composition containing an anti-HSV polynucleotide conjugate is provided. Such a composition is preferably in topically administrable form due to the fact that HSV-1 and HSV-2 are known to cause blister-like conditions, around the mouth in the case of HSV-1 and in the genital area in the case of HSV-2. Thus, compositions such as creams, lotions, ointments, aerosols and skin patches are examples of suitable topically administrable forms of such anti-HSV conjugates. The composition additionally comprises a pharmaceutically acceptable carrier. As used herein, the term "pharmaceutically acceptable" means acceptable for use in the pharmaceutical and veterinary arts, and not being toxic or otherwise unacceptable. The nature of the carrier will of course vary with the intended administrable form.

The present anti-HSV pharmaceutical composition comprises a therapeutically effective amount of the polynucleotide conjugate. The term "therapeutically effective amount" is used herein to denote an amount of the composition indicated for a given treatment while not exceeding an amount which may cause significant adverse effects.

Further, the present composition may also include a second therapeutic agent to enhance the anti-HSV effect thereof. Thus, the composition may be combined with a second compound which is effective against herpes simplex virus in an amount that would amplify the effect of the polynucleotide conjugate when administered alone. An example of a suitable anti-HSV compound for combination with the present polynucleotide conjugate is the guanine analogue, acyclovir, obtainable from Wellcome.

In another aspect of the present invention, the present polynucleotide conjugates may be used as a diagnostic tool. Thus, a biological sample, including for example, blood, urine or saliva, may be analyzed using a polynucleotide conjugate for the presence of HSV-1 or HSV-2. Specifically, an aliquot of the biological sample to be analyzed is combined with a culture of cells normally killed by the virus, e.g. vero cells, to provide a control. Another aliquot of the biological sample is combined with a culture of the HSV-sensitive cells along with an anti-HSV polynucleotide conjugate to provide a test sample. The control and test sample are incubated under suitable growth conditions, and are subsequently analyzed for growth of the cells therein using methods well-established in the art. If the biological sample is virally infected, the cells of the control will be killed by the virus, whereas, in contrast, the anti-HSV conjugate will inhibit the virus in the test sample allowing cell growth to occur.

Specific embodiments of the present invention are described in the following examples which are not to be construed as limiting:

EXAMPLE 1—DIMETHOXYTRITYLATION OF LINKERS

As a first step in adapting diol linker for incorporation via automated polynucleotide synthesis, one of the terminal hydroxyl groups was first protected using a dimethoxytrityl group as follows:

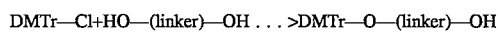

DMTr—Cl+HO—(linker)—OH . . . >DMTr—O—(linker)—OH

The protection procedure is generally applicable for any diol linker, and the various specific steps of the reaction are described below:

(i) 10–30 mmol of the diol compound was co-evaporated with anhydrous pyridine (3×20 ml). The residue was then dissolved in fresh dry pyridine (50–150 ml) to yield a final diol concentration of about 1 mmol/5 ml).

(ii) 4,4'-dimethoxytrityl chloride (6.7–20 mmol) was then added in small portions. The ratio between DMTr-Cl and diol was 1:1.5 eq.

(iii) The reaction was followed at room temperature by thin layer chromatography (TLC) (MeOH/CHCl$_3$, 1:9, v/v) until the appearance of a product spot that was intense relative to remaining DMTr-Cl. The reaction was usually complete after 2–4 hours. The DMTr derivatives were visualized as red-orange spots using an acidic spray (60% aqueous perchloric acid/ethanol, 3:2, v/v).

(iv) When the reaction was complete, 20–30 ml of MeOH was added to quench excess DMTr and the mixture was stirred for an additional 15 minutes.

(v) The solution was then concentrated to a syrup and the residue was resuspended into 50– 150 ml of CHCl$_3$. The chloroform phase was then washed once with 5% NaHCO$_3$ (25–75 ml), and twice with saturated NaCl solution. The aqueous phase was back-extracted with CHCl$_3$ (25–75 ml). The organic phases were combined and dried over anhydrous sodium sulphate. After filtration, the solution was evaporated down to an oily residue under reduced pressure.

(vi) The oily residue was purified by flash chromatography on silica gel. The column was first eluted with petroleum ether/EtoAc (5:1, v/v) followed by elution with petroleum ether/EtoAc (2:1, v/v).

(vii) Fractions containing the final product were combined together and the solvent was removed to yield a residue that was dried overnight under vacuum. Yields, based on the amount of DMTr—Cl used, ranged from 60 to 80%. Products are characterized by standard methods, such as NMR spectroscopy and/or elemental analysis.

In this manner, the following tritylated diol linkers were obtained from the reagents noted below:

(A): DMTr—O—(CH$_2$)$_9$—OH, yield 76.4% from 1,9-nonanediol [3.6 g (22.5 mmol)]; DMTr-Cl [5.0 g (15 mmol)]; and pyridine [100 ml].

(B) : DMTr—O—(CH$_2$)$_2$—O—(CH$_2$)$_2$—O(CH$_2$)$_2$—OH, yield 68.2% from triethylene glycol [3.4 g (22.5 mmol)]; DMTr-Cl [5.0 g (15 mmol)]; and pyridine [100 ml].

(C): DMTr—O—(CH$_2$)$_3$—OH, yield 67.0% from 1,3-propanediol [1.7 g (22.5 mmol)]; DMTr—Cl [5.0 g (15 mmol)]; and pyridine [100 ml].

(D) DMT—O—(CH₂CH₂O)₅—CH₂CH₂—OH, yield 68.4% from hexaethylene glycol [6.35 g (22.5 mmol)], DMT–Cl [5 g (15 mmol)], and pyridine (100 ml).

EXAMPLE 2—PHOSPHITYLATION OF TRITYLATED LINKERS

The tritylated linker prepared as described in Example 1 was next derivatized at the remaining hydroxyl group to incorporate a phosphoramidite group, according to the reaction scheme and description provided below:

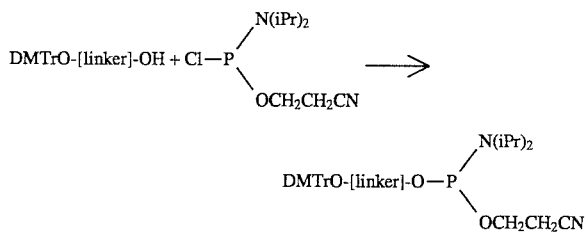

(i) The tritylated product obtained from previous preparations (1–5 mmol) was dissolved in dry THF (10–50 ml). Anhydrous diisopropylethylamine (DIPEA) (4–20 mmol, 4 eq.) was injected under a weak flow of argon.

(ii) The phosphitylating reagent 2-cyanoethyl-N,N-diisopropylchlorophosphoramidite (2–10 mmol, 2 eq., Aldrich Chemical Co.) was then added with a syringe over a period of 2–5 minutes. A white precipitate was quickly formed.

(iii) The reaction mixture was stirred at room temperature for 1–2 hours and monitored by TLC (EtOAc/CH₂Cl₂/TEA, 45:45:10, v/v).

(iv) When the reaction had gone to completion, the excess phosphitylating reagent was quenched by adding several ice cubes. The mixture was diluted with ethyl acetate (50–250 ml) and triethylamine (1–5 ml). The solution was then transferred to a separatory funnel and extracted twice with 10% aqueous sodium carbonate and twice with saturated aqueous sodium chloride.

(v) The organic phase was dried over anhydrous sodium sulphate, filtered, and then evaporated to dryness under reduced pressure.

(vi) The residue was purified by flash chromatography on silica gel using petroleum ether/EtOAc/TEA (20:10:1, v/v) as eluant.

(vii) Fractions containing pure product were combined, evaporated and then dried overnight under high vaccum to remove traces of triethylamine. The product was stored at –20° C. Yield of the isolated product varied from 65 to 80%. Product was characterized by standard methods, such as ¹H-NMR ³¹P-NMR, and elemental analysis.

In this manner, and using the tritylated products of example 1 as starting material, there were prepared the following linkers suitable for coupling between nucleotides via the phosphoramidite approach:

Linker A: DMT—O—(CH₂)₉—O-phosphoramidite TLC (silica gel, petroleum ether/EtOAc/TEA, 50:10:1, v/v/v): $R_f$ 0.84, ¹H-NMR CDCl₃, 500 MHz): δ 1.14–1.62 [26H, m, CH₂, CH(CH₃)₂]; 2.63 (t, 2H, J= 6.5 Hz, CH₂CN); 3.02 (t, 2H, J=6.5 Hz, DMTOCH₂); 3.54–3.88 [2 m with one s centred at 3.78, 12H, OCH₃, CH₂OP, POCH₂CH₂CN, NCH(CH₃)₂]; 6.79–6.84 (m, 4H, arom. H ortho of OCH₃); 7.17–7.45 (m,9H, arom.H). ³¹P-NMR (CDCl₃,121 MHz): 122.4 ppm.

Linker B: DMT—O—(CH₂CH₂O)₂—CH₂CH₂—O—phosphoramidite TLC (silica gel, petroleum ether/EtOAc/TEA, 50:10:1, v/v/v): $R_f$ 0.48, ¹H-NMR (CDCl₃, 500 MHz): δ 1.13–1.18 [12H, 2d, CH(CH₃)₂]; 2.51–2.64 (m, 2H, CH₂CN); 3.23 (t, 2H, J=5 Hz, DMTOCH₂); 3.56–3.86 [m, 20H, OCH₃, OCH₂CH₂O, CH₂OP, POCH₂CH₂CN, NCH(CH₃)₂]; 6.77–6.86 (m, 4H, arom. H ortho of OCH₃); 7.18–7.47 (m, 9H, arom. H). ³¹P-NMR (CDCl₃, 121 MHz): 148.6 ppm.

Linker C: DMT—O—(CH₂)₃-O-phosphoramidite TLC (silica gel, petroleum ether/EtOAc/TEA, 50:10:1, v/v/v): $R_f$ 0.79, ¹H-NMR (CDCl₃, 500 MHz): δ 1.00–1.30 [12H, 2d, CH(CH₃)₂]; 1.89–1.97 (m, 2H, CH₂CH₂CH₂); 2.44–2.51 (m, 2H, CH₂CN); 3.14–3.19 (m, 2H, DMTOCH₂); 3.50– 3.88 [m, 12H, OCH₃, CH₂OP, POCH₂CH₂CN, NCH(CH₃)₂]; 6.74–6.84 (m, 4H, arom. H ortho of OCH₃); 7.14–7.47 (m, 9H, arom. H). ³¹P-NMR (CDCl₃, 121 MHz): 147.3 ppm.

Linker D: DMT—O—(CH₂CH₂O)₅—CH₂CH₂—O-phosphoramidite TLC (silica gel, petroleum ether/EtOAc/TEA, 50:10:1, v/v/v): $R_f$ 0.12, ¹H-NMR (CDCl₃, 500 MHz):δ 1.15–1.21 [12H, 2d, CH(CH₃H)₂]; 2.57–2.66 (m, 2H, CH₂CN 3.23 (t, 2H, J=5 Hz, DMTOCH₂); 3.56–3.91 [m, 32H, OCH₃, OCH₂CH₂O, CH₂OP, POCH₂CH₂CN, NCH(CH₃)₂]; 6.76–6.85 (m, 4H, arom. H ortho of OCH₃); 7.16–7.48 (m, 9H, arom. H). ³¹P-NMR (CDCl₃, 121 MHz): 148.6 ppm.

EXAMPLE 3—GENERAL PROCEDURE FOR LINEAR POLYNUCLEOTIDE CONJUGATE SYNTHESIS

Controlled pore glass (CPG) was used as the solid support matrix for both DNA & RNA synthesis. Polydeoxyribonucleotides (DNA) were prepared by the CE-phosphoramidite method on an Applied Biosystems 391 EP synthesizer (0.15 micromole scale). Cleavage and deprotection were effected by standard ammonia treatment. Oligoribonucleotides (RNA) were prepared according to the method of Usman et al, 1987, J. Am. Chem. Soc., 109, 7845–7854, employing 5'-dimethoxytrityl-2'-t-butyldimethoxysilyl ribonucleoside-3'-CE-phosphoramidites (Peninsula Labs, Calif. or ChemGenes Corp., Mass.). Syntheses were carried out on an Applied Biosystems 380B synthesizer using a modified 0.2 micromole cycle. Cleavage from the support, base & phosphate deprotection, and removal of the 2'-TBDMS groups were performed by established procedures (Scaringe et al, 1990, Nucl. Acids Res., 18, 5433–5441). The crude oligonucleotide in TBAF solution was desalted on a C₁₈ Sep-Pak cartridge prior to purification.

The linker phosphoramidite (dissolved in dry acetonitrile, 0.2–0.3M) was coupled to the support-bound polynucleotide at the desired location, using the synthesis cycle conventional for standard nucleoside phosphoramidites.

In one synthesis cycle, the DMTr protecting groups were removed from the extended oligomer with 2.5% dicholoroacetic acid/dichloromethane. After several washes (acetonitrile is the only solvent used for all washes), cyanoethyl protected nucleoside phosphoramidites (0.12M in dry acetonitrile) were coupled to the support in the presence of 0.5M tetrazole. The coupling time for DNA oligomers was 15 sec (ABI 391EP) and 2×6 minutes for RNA oligomers (ABI 380B). Double couplings were used for RNA synthesis since these phosphoramidites are much less reactive than their DNA homologs. This is followed by capping of the unreacted hydroxy groups (Ac₂O/DMAP), and oxidation of the phosphite triesters to the phosphates (I₂/H₂O). The cycles were repeated until the desired polynucleotide conjugate was obtained. The conjugate was then cleaved from the CPG support by treatment with concentrated ammonia for one hour at room temperature. Deprotection of DNA conjugates and of RNA conjugates was achieved by incubation in ammonia at 55° C. for 6–16 hours. For RNA conjugates specifically, deprotection was performed with ammonia in ethanol (3:1), and a final treatment involved incubation in 1M TBAF at room temperature. The average coupling yield, as assayed by trityl measurement, was 97–99% for DNA oligos, and 95–97% for RNA oligos.

A summary of the protocols used in RNA conjugate synthesis is provided in Table 1 below, for convenience:

TABLE I

Synthetic cycle for the preparation of linker-derivatized TAR oligoribonucleotides

| STEP | REAGENT OR SOLVENT | PURPOSE | TIME (sec) |
|---|---|---|---|
| 1 | Dichloroacetic acid in CH₂Cl₂ (2.5:97.5; v/v) | Detritylation | 5 × 20 |
| 2 | Anhydrous CH₃CN | Wash | 90 |
| 3 | Activated phosphoramidites in anhydrous CH₃CN* | Coupling | 2 × 360 |
| 4 | Anhydrous CH₃CN | Wash | 20 |
| 5 | HPLC grade CH₂Cl₂ | Wash | 20 |
| 6 | Anhydrous CH₃CN | Wash | 20 |
| 7 | DMAP/THF (6.5 g: 94 ml) Ac₂O/Lutidine/THF (1:1:8; v/v/v) | Capping | 60 |
| 8 | 0.1M I₂ in THF/Lutidine/H₂O (160:40:4; v/v/v) | Oxidation | 60 |
| 9 | Anhydrous CH₃CN | Wash | 3 × 20 |

*The coupling reactions were carried out by premixing 0.5M tetrazole with 0.15–0.30M standard or modified phosphoramidites in anhydrous CH₃CN.

The crude deprotected polynucleotide conjugates were purified by standard electrophoresis methods (Atkinson & Smith, in (1984) "Oligonucleotide Synthesis: A Practical Approach" (Gait, M. J.; ed.) IRL Press, Oxford/Washington, D.C.)using 15–20% polyacrylamide/7M urea gels. The bands were visualized by UV shadowing and the product was cut out and eluted from the gel. The eluted conjugate was finally desalted on a C₁₈ Sep-Pak and quantitated by OD₂₆₀.

Each oligonucleotide linker conjugate was checked for homogeneity and "sized" by 5'-$^{32}$P-end labeling/analytical PAGE against the crude material and oligonucletide markers. These RNA oligomers were further characterized by enzymatic RNA sequencing [Donis-Keller, H. (1980) Nucleic Acids Res., 8, 3133–3142] or base-composition analysis [Seela, F. & Kaiser, K. (1987) Nucleic Acids Res., 15, 3113–3129].

EXAMPLE 4—PLAQUE REDUCTION ASSAY USING POLYNUCLEOTIDE CONJUGATE OF FORMULA (III)

Vero cells (African green monkey kidney cells, ATCC CCL 81) were seeded into a 96-well plate at a concentration of 2×10⁴ cells per well in 50 μl of Dulbecco's modified eagle medium (DMEM, Gibco). The media was supplemented with 10% Nu-serum (Biomedical Products), penicillin (100 IU/ml), streptomycin (100 μl/ml) and gentamicin (0.02 mg/ml) obtained from Gibco. The cells were pretreated with polynucleotide conjugate (III) at concentrations of 1 μM and 10 μM by incubation for 24 hours at 37° C. and 5% CO₂. Following the incubation, the culture medium was removed from the cells.

To the cell monolayers was added HSV-1 (ATCC 733-VR), diluted with DMEM containing 2% Nu-serum, using a serial 10-fold dilution method to result in concentrations of 100, 10 and 1 PFU (plaque forming units) per well, respectively. The infected cells were incubated at 37° C. for 1 hour at 5% CO₂ to allow viral adsorption to occur. The virus inocula was then removed from the wells and replaced with 0.1 ml of DMEM supplemented with 2% Nu-serum and containing the appropriate concentration of polynucleotide conjugate (III). The cells were incubated for two days, i.e. until an 80%–90% cytopathic effect was observed in the viral control wells, wells containing infected cells and no conjugate (III).

The media was removed from the cells and the cells were subsequently stained with crystal violet in 70% ethanol:formalin:acetic acid (20:2:1) solution and heat fixed. The average number of plaques per well of each test sample were counted using a dissecting microscope (10–40× magnification). Inhibition was determined as the difference between the number of plaques in the control sample (0 μM conjugate) and the number of plaques in the test sample.

The following chart indicates an estimation of the inhibitory effect of conjugate (III) on the HSV-1 replication:

| Conc'n Conjugate (III) | % Inhibition |
|---|---|
| 1 μM | 25% |
| 10 μM | 50% |

EXAMPLE 5—PLAQUE REDUCTION ASSAY USING POLYNUCLEOTIDE CONJUGATE OF FORMULA (IV)

Vero cells were subjected to a plaque reduction assay as described in Example 4 except conjugate (III) was replaced with polynucleotide conjugate (IV). The following results were obtained using conjugate (IV):

| Conc'n Conjugate (IV) | % Inhibition |
|---|---|
| 1 μM | 50% |
| 10 μM | 55% |

EXAMPLE 6—PRODUCTION OF RNA POLYNUCLEOTIDE CONJUGATES

The RNA structure known as Tar consists of 59 bases in most HIV-1 isolates, arranged in a stem-loop structure with two or three bulges in the stem. Previous studies have shown however that the full length Tar structure can be reduced significantly in size to a 27-mer (FIG. 4, SEQ ID NO:4) while retaining full tat-binding activity (Sumner-Smith et al, J. Virol., 1991, 65:5196.

Figure 4:
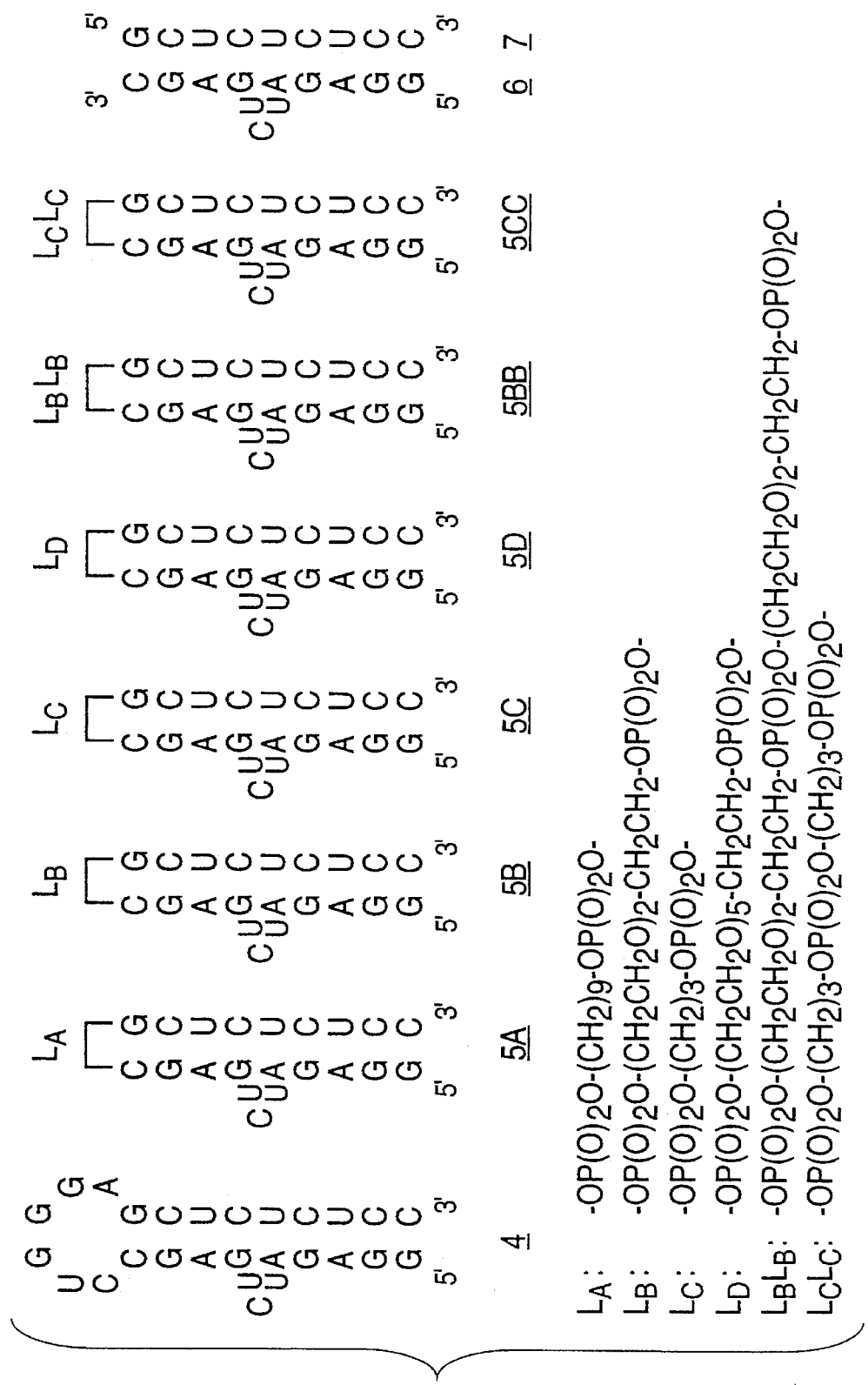
FIGS. 4–7 illustrate the structure of specific polynucleotide conjugates (SEQ ID NOS. 4, 5 and 3 are shown in these Figures, respectively)

Various linear polynucleotide conjugates, representing analogues of a 27-mer truncated version of Tar (FIG. 4, SEQ ID NO:4) were synthesized and evaluated. All were prepared using the synthesis procedures previously described hereinabove. As FIG. 4 illustrates, the linear polynucleotide conjugates tested comprised two classes; one class in which the 6-mer loop in the Tar analogue (4) was replaced by each of four different linkers (conjugates 5A, 5B, 5C and 5D which each include nucleotides 1-13 of SEQ ID NO:4) and another class in which the 6-mer loop was replaced by two coupled linkers (5BB and 5CC which each include nucleotides 1-12 of SEQ ID NO:4). The stability and tat binding properties of these oligonucleotides were determined and compared, and the results are shown in Table 2 below.

Melting temperature (Tm) measurements were carded out in 100 mM NaCl/10 mM sodium phosphate buffer (pH 7.0). Samples were heated from 25° to 85° C. in 1° C. increments using a HP 8459 UV/VIS spectrophotometer and a HP 89100A temperature controller. The concentration of nucleic acid was 2.5–3.0 μM, and absorbance was monitored at 260 nm. $T_m$ values were determined by a first-derivative plot of absorbance vs temperature. Each experiment was performed in duplicate and the average reported as the thermal denaturation temperature.

Ligand binding of the oligonucleotides was assessed by gel electrophoresis and RNA mobility shift assay. Linker-derivatized oligoribonucleotides (5A–5CC) and the control sequences (4, 6 and 7, FIG. 4, SEQ ID NO:4, nucleotides 1–12 of SEQ ID NO:4 and nucleotides 19–27 of SEQ ID NO:4, respectively) were 5'-$^{32}$P-labeled with T4 polynucleotide kinase and [γ-$^{32}$P]ATP. The labeled oligomers were then purified by phenol/chloroform extraction/EtOH precipitation or spin-column filtration (Bio-Rad, Bio-Spin 30). Prior to binding assays, the RNAs were dissolved in 20 mM Tris-HCl (pH 7.5)/100 mM NaCl, heated to 85° C. for 3 min, then slow-cooled to room temperature. Binding assays were carried out in 20 μl reaction mixtures containing 10 mM Tris-HCl (pH 7.5), 50 mM NaCl, 1 mM DTT, 1 mM EDTA, 0.5 U/ml RNAsin (Promega), 0.09 μg/ml BSA, 5% (v/v) glycerol, 0.1 nM $^{32}$P-labeled RNA (2000–5000 cpm) and either peptide derived from the HIV-1 Tat protein RKKRRQRRRPPQGS (SEQ ID NO:1(amino acids 49–62 of HIV LAI isolate) (Weeks et al., Science, 1990, 249:1281; Delling et al., Proc. Natl. Acad. Sci., 1991, 88:6234) (American Peptide Co., Santa Clara, Calif.) or full-length Tat protein (American Bio-Technologies, Inc.) at a concentration of 0.5 pM to 1000 nM (Roy et al., Genes Dev., 1990, 4:1365). The reactions were incubated at 23° C. for 25 min, chilled on ice for 5 min, then loaded on 5% native polyacrylamide gels (acrylamide:bis-acrylamide=30:0.8, w/w) containing 5% glycerol. The gels were pre-run for 15 min prior to loading, then run for 2.5 h at a constant current of 30 mA at 4° C. in 0.5' TBE buffer. The gels were dried onto DEAE paper (Whatman DE81) and exposed to Kodak X-Omat X-ray film with an intensifying screen overnight at −70° C. Competition binding experiments were carried out as described above except that the concentration of Tat protein was kept constant at 100 nM and unlabeled competitor RNA was added in a concentration range of 0.9 nM to 5000 nM.

TABLE II

Thermodynamic and binding properties of TAR analogues

| Oligomer | Substitution | $T_m$ (°C.) | ($K_d$) | Binding (%) |
|---|---|---|---|---|
| 4 | 6-nt loop (wt sequence) | 60 | +(0.41) | 45.9 |
| 5A | linker A loop | 61 | +(0.71) | 40.1 |
| 5B | linker B loop | 58 | +(0.95) | 42.6 |
| 5C | linker C loop | 56 | − | − |
| 5D | linker D loop | 63 | +(0.66) | 56.0 |
| 5BB | 2 X linker B/loop | 59 | +(1.13) | 38.3 |
| 5CC | 2 X linker C/loop | 56 | +(0.43) | 17.8 |

TABLE II-continued

Thermodynamic and binding properties of TAR analogues

| Oligomer | Substitution | $T_m$ (°C.) | ($K_d$) | Binding (%) |
|---|---|---|---|---|
| 6 + 7 | without connection | 32 | − | |

$K_d$ values are expressed in nanomolar concentrations: (+) strong binding; (−) no binding
Binding capacity indicates the % of active RNA molecules capable of binding to peptide upon saturation The thermal denaturation experiments indicated that every linker-derivatized TAR analogue had some secondary structure. With the exception of structure 5C which incorporates a linker expected to be too short to allow proper duplex formation, binding assays revealed tat-binding function in the conjugated duplexes versus the unlinked controls. Similar binding was also confirmed in experiments using the full length tat protein.

Further evaluation of linker incorporation has indicated that relatively short linkers can be used to advantage, to replace nucleotides resident in the polynucleotide strands, e.g. to replace nucleotides in the bulge of TAR. In particular, a Tar conjugate was produced in which the bulge 5'—U—C—U—3' was replaced by the structure 5'—U—L$_c$—L$_c$—3', to yield structure 8 (Kd=0.51 nM, Tm=60° C.)) shown below (which includes bases 19–27 of SEQ ID NO:4:

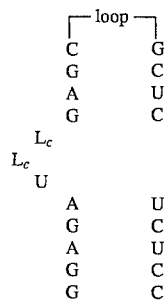

8 where LcLc is —O—(CH$_2$)$_3$—O—PO$_2$13 O—(CH$_2$)$_3$—O—.

Tat-binding analysis of the resulting structure has shown that replacement of nucleotides within the bulge preserved the tat-binding structure of TAR. Thus, in certain instances, linkers equivalent in length to C$_3$ can be used, particularly within the so-called bulge structures which form at non-annealed sites of duplex structures.

Moreover, studies with a short un-linked duplex (oligomer 6+7, nucleotides 1–12 and 19–27, respectively, of SEQ ID NO:4) of same length have shown that this duplex has a significant lower $T_m$ (32° C.) when compared to its linked counterparts (56°–63° C.), and it also failed to form any effective complexes with Tat-derived peptide, probably due to its thermal instability. This provides strong evidence that synthetic linkers add substantial stability to the un-linked duplex structures to a such degree that their normal biological functions, such as binding to proteins, can be maintained.

In another experiment, there was successfully generated a particular Tar analog where the linker was incorporated at the bottom of of the duplex (oligomer 9, below, which includes SEQ ID NO:2).

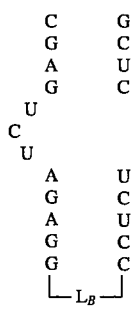

9

Both $T_m$ measurements ($T_m$=61° C.) and binding assays ($K_d$=2.20 nM) indicated that this analog also retains the physical and binding properties of the wild-type Tar structure.

EXAMPLE 7—BINDING ASSAYS WITH FULL-LENGTH TAT AND COMPETITION EXPERIMENTS

To evaluate possible differences in binding affinity for the short Tat-peptide and full length native Tat protein, the binding affinities of the Tar conjugates for full-length Tat protein (86 amino acids) were assessed using the mobility shift assay. By this method, The $K_d$ value for the full-length Tat (1.17 nM) was slightly higher than that for the Tat-derived peptide (0.71 nM). When Tar conjugate 5B was added to a pre-formed complex between the 27mer fragment of the wild-type Tar stem-loop (oligomer 4, SEQ ID NO:4) and full-length Tat protein, strong competition with the TAR sequence was observed. The complex was totally competed away when the ratio between the Tar conjugate and the Tat protein was 1:1.

EXAMPLE 8—SYNTHESIS OF CYCLIC POLYNUCLEOTIDE CONJUGATES

To synthesize cyclic polynucleotide conjugates, there was applied the general approach of (a) synthesizing the corresponding linear polynucleotide conjugate in the manner described previously herein, and then (b) cyclizing the linear polynulceotide conjugate either via enzymatic ligation (DNA or RNA ligase) or by chemical closure. In particular, the enzymatic ligation approach has been applied to convert linear conjugate 10, to the cyclic TAR conjugate 11(which includes nucleotides 1–12 of SEQ ID NO:4, as shown below:

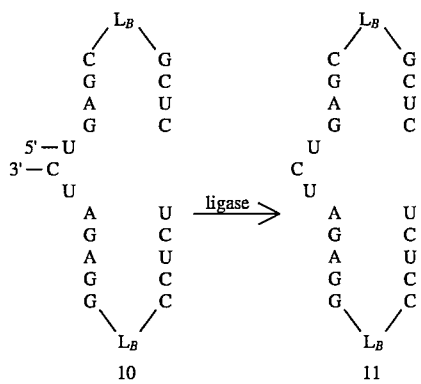

To prepare the cyclic analogue, the linear conjugate 10 was first radiolabelled with gamma $^{32}$P-ATP as described previously herein. The heated T4 polynucleotide mixture was then cooled slowly to room temperature, and 1 µl (10 units) of T4 RNA ligase were then mixed with 10 µl of radiolabelled conjugate, 2 µl of ATP (10 mM) and 7 ul of 1× ligase buffer consisting of 66 mM Tris-HCl (pH 7.5), 6.6 mM MgCl$_2$, 1 mM DTT, and 1 mM ATP. The ligation reaction was pursued for four hours at room temperature.

The ligated product was then purified on a 20% denaturing polyacrylamide gel. The band corresponding to the cyclic conjugate (evident from its faster migration relative to linear conjugates) was cut out and extracted from the gel with 0.3M NaOAc at room temperature overnight. The sodium acetate solution containing the cyclic conjugate was then washed with an equal volume of phenol solution in order to eliminate any proteinaceous contamination. After this step, two volumes of ethanol/acetone (1:1, v/v) solution were added to the aqueous phase, and the mixture was stored at −20° C. overnight. The cyclic conjugate 11 (which includes nucleotides 1–12 of SEQ ID NO:4, was ultimately collected and was dried under high speed vacuum.

EXAMPLE 9—BINDING PROPERTIES OF CYCLIC POLYNUCLEOTIDE CONJUGATES

Figure 6:
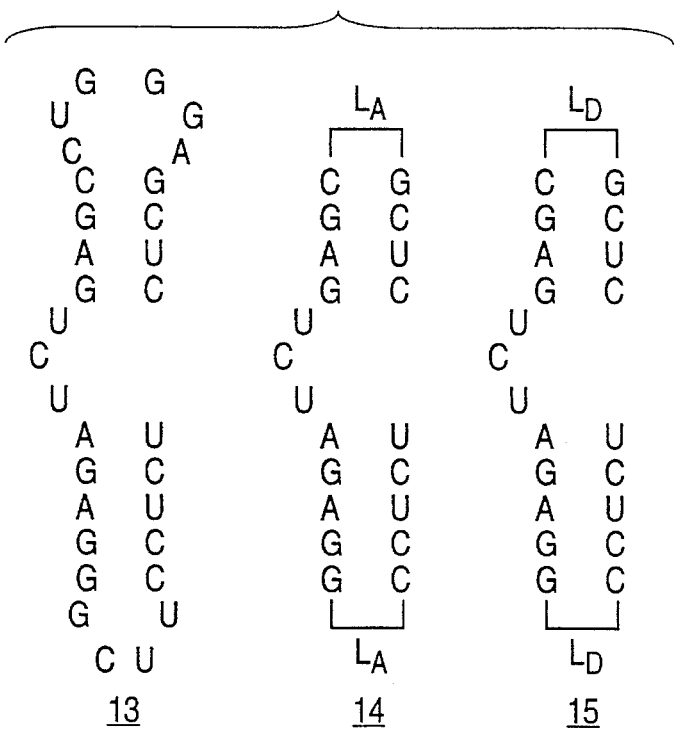

Using the best ligation site identified from the previous example, there was successfully generated a series of Tar conjugates; two of them are illustrated in FIG. 6. Both of these constructs (14 & 15, which each include bases 1–12 of SEQ ID NO:4) are 21-mers and differ only in the chemical linker used to replace the nucleotide loops at the top and bottom of the duplex. Oligomer 14 contains Linker A and oligomer 15 contains linker D. All three cyclic polynucleotide conjugates were subjected to the binding assay as described previously.

It was found that the 31-mer (oligomer 13, SEQ ID NO:5) as well as the linker D cyclic conjugate (oligomer 15, which includes bases 1–12 of SEQ ID NO:4) bind efficiently to both peptide and the full-length Tat protein, although, for reasons that are not clear, no binding was seen with oligomer 14 (which includes bases 1–12 of SEQ ID NO: 4). It is possible that while the length of the chemical linker used does not appear to be significant in the linear series, it may be significant for proper functioning of cyclic polynucleotide conjugates that bind to Tat protein. This suggests that synthetic duplex-stabilizing linkers should have some flexibility in order to allow the mini-duplexes to adopt possible conformational changes upon protein recognitions.

EXAMPLE 10—LIGATION SITE OPTIMIZATION FOR GENERATING CYCLIC CONJUGATES

Figure 5:
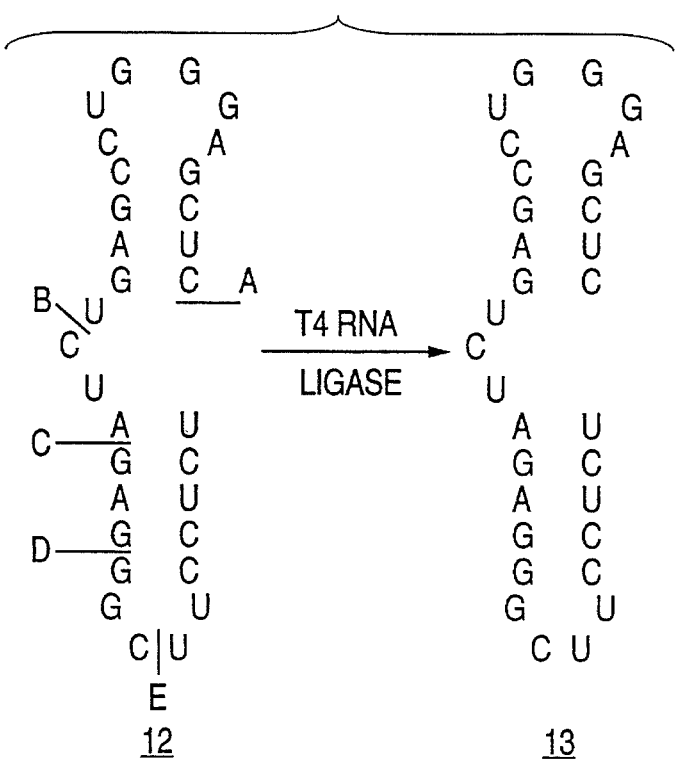

To cyclize the polynucleotide conjugates as efficiently as possible a number of potential ligation sites (a–e) were examined using structure 12 (FIG. 5, SEQ ID NO:5). To prepare this cyclic polynucleotide conjugate, the linear conjugates (one for each ligation site chosen) were synthesized and radiolabelled with gamma $^{32}$P-ATP as described previously herein. 10 µl of each radiolabelled conjugate was added to 2 ul of ATP (10 mM), 2 µl of DMSO(100%), 2 µl of 10× ligase buffer consisting of 500 mM Tris-HCl (pH 7.8). 100 mM MgCl$_2$ 100 mM β-mercaptoethanol, 10 mM ATP, and 1 µl (10 UNITS) of RNA Ligase. The ligation reaction was pursued for 4 hours at 37° C. The ligated products (2 µl of each) were examined by separation on 20% denaturing polyacrylamide and compared directly to an equivalent amount of unligated linear radiolabelled polynucleotide conjugate on the same gel.

From these results, it was determined that ligation site c (between the A and G residue) on the front strand immediately beneath the -UCU- bulge gave the best conversion of linear to cyclic conjugate.

EXAMPLE 11—BINDING PROPERTIES OF CYCLIC POLYNUCLEOTIDE CONJUGATES

Using the best ligation site identified from the previous example, there was successfully generated a series of Tar conjugates; two of them are illustrated in FIG. 6. Both of these constructs (14 & 15, which each include nucleotides 1–12 of SEQ ID NO:4) are 21-mers and differ only in the chemical linker used to replace the nucleotide loops at the top and bottom of the duplex. Oligomer 14 contains Linker A and oligomer 15 contains linker D. All three cyclic polynucleotide conjugates were subjected to the binding assay as described previously.

It was found that the 31-mer (oligomer 13, SEQ ID NO:5) as well as the linker D cyclic conjugate (oligomer 15, which includes bases 1–12 of SEQ ID NO:4) bind efficiently to both peptide and the full-length Tat protein, although, for reasons that are not clear, no binding was seen with oligomer 14 (which includes bases 1–12 of SEQ ID NO:4. It is possible that while the length of the chemical linker used does not appear to be significant in the linear series, it may be significant for proper functioning of cyclic polynucleotide conjugates that bind to Tat protein. This suggests that synthetic duplex-stabilizing linkers should have some flexibility in order to allow the mini-duplexes to adopt possible conformational changes upon protein recognitions.

EXAMPLE 12—IN VITRO STABILITY AND CELL UPTAKE OF POLYNUCLEOTIDE CONJUGATES

Figure 7:
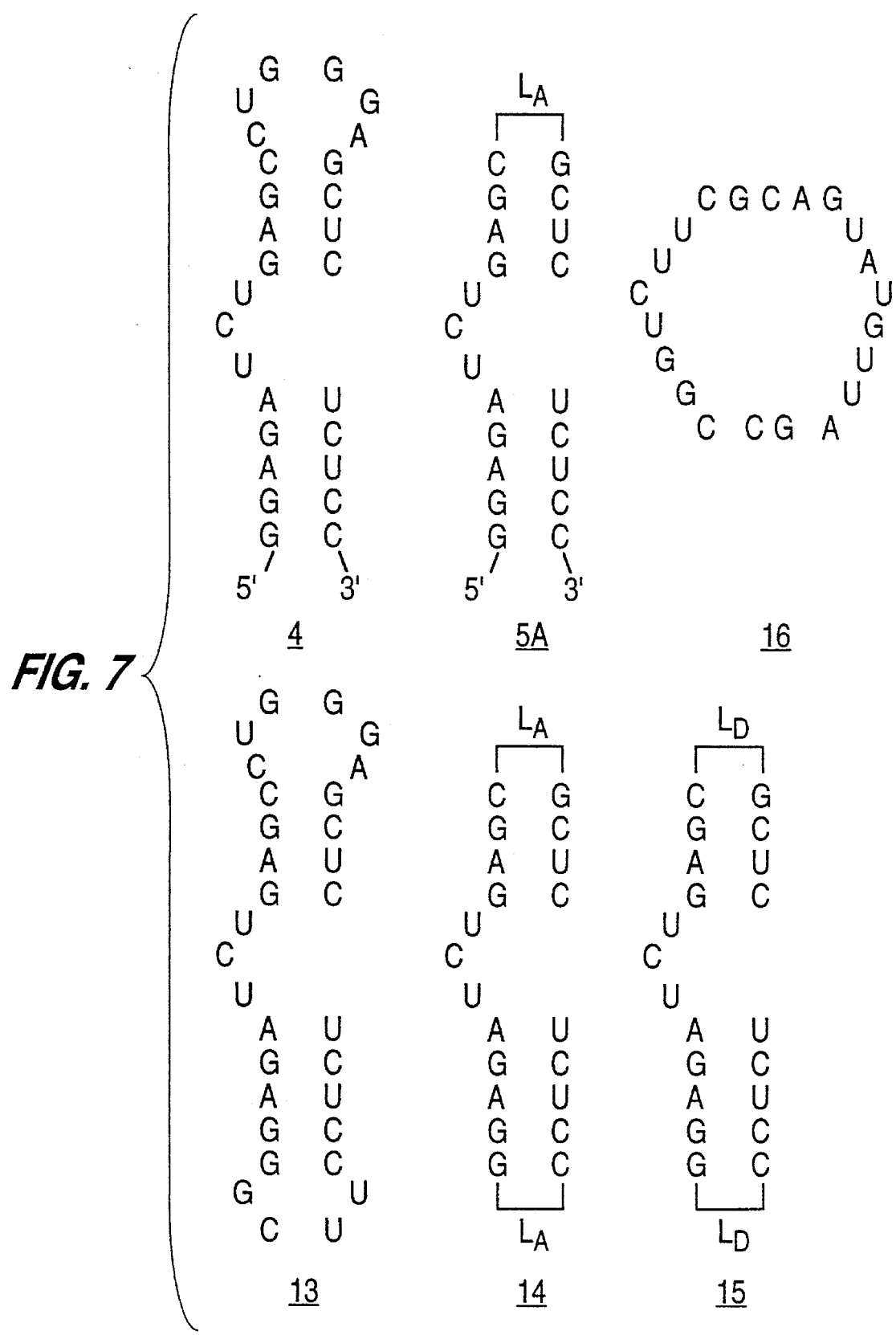

A number of different polynucleotides were used in a comparative analysis of the relative stability of linear versus cyclic conjugates. For these studies the following conjugates were used (FIG. 7). To evaluate conjugate stability further there was also generated a 21-mer RNA oligomer (5'-CUUCGCAGUAUGUUAGCCGGU-3', SEQ ID NO:3) which has the same base composition as the cyclic oligomers 14 & 15 (which each include bases 1–12 of SEQ ID NO:4) but should remain in single-stranded open-circle form due to the non-complementarity between the bases (FIG. 7, oligomer 16, SEQ ID NO:3). Each of the polynucleotide conjugates used was synthesized, radiolabelled, and ligated as previously described herein. After radiolabelling and/or ligation, the polynucleotides were purified on 20% denaturing polyacrylamide gels as previously described. For each of the various conditions, the same amount of radiolabelled gel-purified polynucleotide was used (300,000 CPM). The conditions used for each of the reactions are described below.

Exounuclease III:

300,000 CPM of gel-purified polynucleotide was incubated in the presence of 20 units of Exonuclease III (1 µl) and 1 µl of 10× buffer which consisted of 500 mM Tris-HCl pH 8.0, 50 mM $MgCl_2$, 100 mM β-mercaptoethanol. Enzymatic treatment was pursued for 6 h at 37° C. and a sample was removed for analysis at this time.

Mung Bean Nuclease:

300,000 CPM of gel-purified polynucleotide was incubated in the presence of 5 units of Mung Bean Nuclease (1 µl) and 1 µl of 10× buffer which consisted of 500 mM sodium acetate pH 5,0, 300 mM NaCl, 1 mM $ZnSO_4$. Enzymatic treatment was pursued for 6 h at 37° C. and a sample was removed for analysis at this time.

Calf Intestinal Alkaline Phosphatase:

300,000 of CPM gel-purified polynucleotide was incubated in the presence of 5 units of calf intestinal alkaline phoshatase and 1 µl of 10× buffer which consisted of 500 mM Tris-HCl pH 8.5, and 1 mM EDTA. Enzymatic treatment was pursued for 20 h at 37° C. and a sample was removed at this time.

Cell Extract and Nuclear Extracts:

Cell and nuclear extracts were prepared essentially by the method of Dignam et. al., 1983, Nucl. Acids. Res., 11:1475. The amount of protein in each extract was determined using Bovine Serum Albumin as a standard. 300,000 CPM of gel-purified polynucleotide was incubated in the presence of 8 ug cell extract protein, or 6 µg nuclear extract protein at 37° C. Equivalent samples from both cell and nuclear extract digestions were removed at various times (8 and 24 h).

Samples from all treatments were applied to 20% denaturing polyacrylamide gels and exposed to Kodak X-Omat AR film. The band of interest was excised from the gel and the amount of radioactivity was determined. The relative stability of each treatment was determined by comparing the amount of radioactivity of each sample to the amount of radioactivity of a control sample which was not treated with the same enzyme. Results of these stability studies are presented below:

TABLE III

Stability studies of TAR conjugates

| TREATMENT* | TIME (h) | #4 | #5A | #16 | #13 | #14 | #15 |
|---|---|---|---|---|---|---|---|
| Exonuclease III | 6 | 8.0% | 19% | 14% | 46% | 79% | 84% |
| MUNG BEAN | 6 | 3.0% | 27% | 8.5% | 35% | 49% | 54% |
| CIAP | 24 | + | + | − | − | − | − |
| CELL | 8 | 4.8% | 1.7% | 2.4% | 72% | 73% | 86% |
| EXTRACT | 24 | 0.2% | 0.3% | 0.5% | 34% | 55% | 37% |
| NUC. | 8 | 1.0% | 1.5% | 33% | 83% | 88% | 84% |
| EXTRACT | 24 | 0.1% | 0.3% | 0.5% | 58% | 31% | 32% |

All treatments were carried out at 37° C. Cellular and nuclear extracts were obtained from HEP-2 cells (liver cells).
+ Sensitive to dephosphorylation by CIAP treatment.
− Not sensitive to dephosphorylation by CIAP treatment.
% #of full length molecules remaining These results demonstrate that Tar conjugate 5A has a similar stability as the wild-type sequence (oligomer 4, SEQ ID NO:4) in cellular and nuclear extracts although the conjugate appears far more stable against single strand-specific nucleases such as mung bean nucleases. The duplex-forming cyclic linker molecules (oligomer 14 & 15, which each include nucleotides 1–12 of SEQ ID NO:4) are much more stable than both the linear conjugates and the single-stranded cyclic control (oligomer 16, SEQ ID NO:3).

Cell Uptake Studies

For these studies, 5 pmoles of the Linker A and Linker D conjugates (oligomer 14 & 15 in FIG. 7, which each include bases 1–12 of SEQ ID NO:4) were radiolabelled, ligated, and gel-purified as described previously. For each of these polynucleotides, equivalent amounts of radioactivity were incubated in the presence of Hut-78 (Human T-cells) and at various times, samples were removed and the radioactivity in various fractions was determined. The percentage of uptake was plotted over time and results are shown in FIG. 8 for oligomer 14 and in FIG. 9 for oligomer 15. As the Figures illustrate, approximately 20% of the polynucleotide is cell-associated after 24 hours of incubation.

We claim:

1. A duplex-forming polynucleotide conjugate having the general formula (I):

$$X—L—Y \quad (I)$$

wherein:

X and Y are first and second polynucleotide strands capable of annealing to form an ICP4 protein binding site; and L is a first chemical linker coupled covalently between the 3' end of said first polynucleotide strand and the 5' end of said second polynucleotide strand to form a duplexed ICP4 protein-binding structure.

2. A polynucleotide conjugate as defined in claim 1, wherein said polynucleotide strands consist of deoxyribonucleotides.

3. A polynucleotide conjugate as defined in claim 1, wherein said polynucleotide strands are complementary.

4. A polynucleotide conjugate having the following formula (III), SEQ ID NOS:6 and 7,

5' CGCTATCGTCCATACCGACCAC $L_A$                                                             (III)

3' GCGATAGCAGGTATGGCTGGTG wherein $L_A$ is a chemical linker.

5. A polynucleotide conjugate as defined in claim 4, wherein $L_A$ is HO—$(CH_2)_9$—OH.

6. A polynucleotide conjugate as defined in claim 1, wherein said chemical linker has a length which corresponds to a linear chain alkane having from 4 to 20 carbon atoms.

7. A polynucleotide conjugate as defined in claim 6, wherein said chemical linker has a length which corresponds to a linear chain alkane having from 8 to 15 carbon atoms.

8. A polynucleotide conjugate as defined in claim 7, wherein said chemical linker has a length which corresponds to a linear chain alkane having from 9 to 12 carbon atoms.

9. A polynucleotide conjugate as defined in claim 1, wherein a second chemical linker is coupled covalently between the 5' end of said first polynucleotide strand and the 3' end of said second polynucleotide strand.

10. A polynucleotide conjugate comprising first and second complementary polydeoxyribonucleotide strands which are capable of annealing to form a herpes simplex virus ICP4 binding site, wherein the 3' terminus of said first polydeoxyribonucleotide strand is coupled covalently the 5' terminus of said second polydeoxyribonucleotide strand.

11. A composition comprising a polynucleotide conjugate as defined in claim 1, and a carrier.

12. A composition comprising a polynucleotide conjugate as defined in claim 10, and a carrier.

13. A method of diagnosing a herpes simplex virus infection in a mammal comprising the steps of:

combining a biological sample from said mammal with a culture of cells sensitive to herpes simplex virus to provide control and test samples;

adding to said test sample but not to said control sample a polynucleotide conjugate as defined in claim 1;

incubating said control and test samples under conditions appropriate for cell growth; and determining the viability of the cells in the control and test samples, wherein cell death in said control sample greater than in said test sample indicates herpes simplex virus infection in said mammal.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 14 amino acids
    ( B ) TYPE: amino acid
    ( D ) TOPOLOGY: linear ( x i ) SEQUENCE DESCRIPTION: SEQ ID NO:1:

Arg Lys Lys Arg Arg Gln Arg Arg Arg Pro Pro Gln Gly Ser
  1               5                   10

( 2 ) INFORMATION FOR SEQ ID NO:2:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

CGAGUCUAGA GG                                                                 12

( 2 ) INFORMATION FOR SEQ ID NO:3:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

CUUCGCAGUA UGUUAGCCGG U                                                       21

( 2 ) INFORMATION FOR SEQ ID NO:4:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

GGAGAUCUGA GCCUGGGAGC UCUCUCC                                                 27

( 2 ) INFORMATION FOR SEQ ID NO:5:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

UCUCCUUCGG GAGAUCUGAG CCUGGGAGCU C                                            31

( 2 ) INFORMATION FOR SEQ ID NO:6:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear (  x i  ) SEQUENCE DESCRIPTION: SEQ ID NO:6:

CGCTATCGTC CATACCGACC AC                                                    22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTGGTCGGTA TGGACGATAG CG                                                    22

( 2 ) INFORMATION FOR SEQ ID NO:8:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CGGTATGGAC GAT                                                              13

( 2 ) INFORMATION FOR SEQ ID NO:9:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATCGTCCATA CCG                                                              13